(12) United States Patent
Nishikawa et al.

(10) Patent No.: US 8,828,714 B2
(45) Date of Patent: Sep. 9, 2014

(54) METHOD OF EVALUATING ELIMINATION OF MICROORGANISMS AND APPARATUS FOR EVALUATING ELIMINATION OF MICROORGANISMS

(75) Inventors: Kazuo Nishikawa, Osaka (JP); Hisaharu Yagi, Osaka (JP); Yoshihiro Shimizu, Osaka (JP); Tetsuyuki Ohtani, Osaka (JP); Hideo Nojima, Osaka (JP); Masato Aoki, Osaka (JP); Miyuki Aoki, legal representative, Chigasaki (JP)

(73) Assignee: Sharp Kabushiki Kaisha, Osaka-shi (JP)

( * ) Notice: Subject to any disclaimer, the term of this patent is extended or adjusted under 35 U.S.C. 154(b) by 0 days.

(21) Appl. No.: 13/495,964

(22) Filed: Jun. 13, 2012

(65) Prior Publication Data

US 2012/0315626 A1    Dec. 13, 2012

Related U.S. Application Data

(63) Continuation of application No. 10/510,210, filed as application No. PCT/IB03/01250 on Apr. 7, 2003.

(30) Foreign Application Priority Data

Apr. 5, 2002   (JP) ................. 2002-104306
Nov. 8, 2002   (JP) ................. 2002-326078
Apr. 4, 2003   (JP) ................. 2003-102054

(51) Int. Cl.
*C12M 1/34* (2006.01)
*A61L 2/28* (2006.01)
*C12Q 1/22* (2006.01)
*A61L 9/18* (2006.01)
*A61L 2/00* (2006.01)
*C12M 1/12* (2006.01)
*A61L 9/22* (2006.01)

(52) U.S. Cl.
CPC ... *C12Q 1/22* (2013.01); *A61L 9/18* (2013.01); *A61L 2/0029* (2013.01); *A61L 2/28* (2013.01); *C12M 37/06* (2013.01); *A61L 9/22* (2013.01); *A61L 2/0011* (2013.01)

USPC ................. 435/287.4; 435/303.1; 435/309.1; 435/31

(58) Field of Classification Search
None
See application file for complete search history.

(56) References Cited

U.S. PATENT DOCUMENTS 5,501,084 A * 3/1996 Chang et al. ................... 62/264
5,639,452 A   6/1997 Messier (Continued)

FOREIGN PATENT DOCUMENTS

AU   9349401 A    4/2002
EP   660668 A1   7/1995

(Continued)

OTHER PUBLICATIONS

Akiyama et al., "Efficacy of Microorganisms Filtration with Air Filter," 2003, pp. 58-63.

(Continued)

*Primary Examiner* — William H Beisner
(74) *Attorney, Agent, or Firm* — Birch, Stewart, Kolasch & Birch, LLP.

(57) ABSTRACT

The sterilizing effect of particle irradiation on microorganisms for the sterilizing treatment thereof can be evaluated. The evaluation can be done by supplying microorganisms in the space inside a container (8), allowing particles (7) for the sterilizing treatment of microorganisms to irradiate the microorganisms, sampling the microorganisms by a sampling means (6) after the irradiation of the particles (7) and measuring the sampled microorganisms. The microorganisms as the subject for the sterilizing treatment can be a combination of one or more members selected from the group consisting of bacteria, mycete, viruses and allergens. As the particles, for example, positive ions, negative ions, and gases of positive ions and negative ions in mixture, charged particles such as α rays and β rays, various plasma gas particles, particles such as ozone and radical particles, and particles of chemical agent can be used.

10 Claims, 23 Drawing Sheets

(56) References Cited

U.S. PATENT DOCUMENTS

| | | |
|---|---|---|
| 6,171,548 B1 | 1/2001 | Rose et al. |
| 2002/0014401 A1 | 2/2002 | Fleischer |
| 2007/0092928 A1 | 4/2007 | Nishikawa |

FOREIGN PATENT DOCUMENTS

| | | |
|---|---|---|
| EP | 1293216 A1 | 3/2003 |
| JP | 5-322218 A | 12/1993 |
| JP | 8-501300 A | 2/1996 |
| JP | 2001-231543 A | 8/2001 |
| JP | 2001-327855 A | 11/2001 |
| JP | 200172069 A | 11/2001 |
| JP | 2002-58731 A | 2/2002 |
| JP | 2002-65838 A | 3/2002 |
| JP | 2002-75588 A | 3/2002 |
| JP | 2002-75590 A | 3/2002 |
| JP | 2003-325198 A | 11/2003 |
| KR | 10-0738174 A | 7/2007 |
| NZ | 255299 A | 12/1996 |
| WO | WO 94/06296 A1 | 3/1994 |
| WO | WO 01/87364 A1 | 11/2001 |
| WO | WO 0217978 A1 * | 3/2002 |
| WO | WO 2004/074832 A1 | 9/2004 |

OTHER PUBLICATIONS

Japanese Office Action which issued in Japanese application No. 2003-102054 on Nov. 7, 2007, English translation is attached.

JPO International Search Report for Appl. No. PCT/IB03/01250 dated Jun. 24, 2003.

Menzies et al., "Germicidal ultraviolet irradiation in air conditioning systems: effect on office worker health and wellbeing: a pilot study," Occup. Environ. Med., 1999, vol. 56, pp. 397-402.

Osawa, excerpt from trial decision by Fair Trade Commission for, 2001, pp. 2-43.

USPTO Office Action dated Apr. 14, 2010 for U.S. Appl. No. 10/510,210.

USPTO Office Action dated Dec. 7, 2009 for U.S. Appl. No. 10/510,210.

USPTO Office Action dated May 29, 2009 for U.S. Appl. No. 10/510,210.

* cited by examiner

Fig. 5
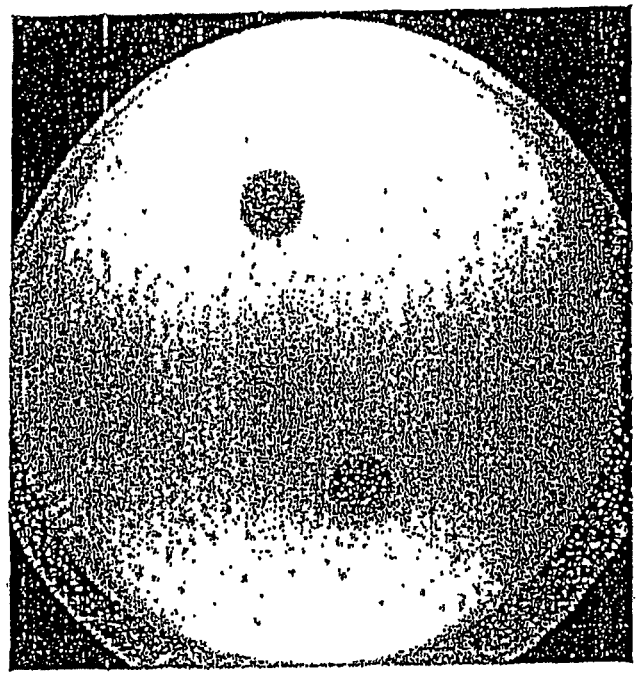
No ion discharge (15 min after)
(b)
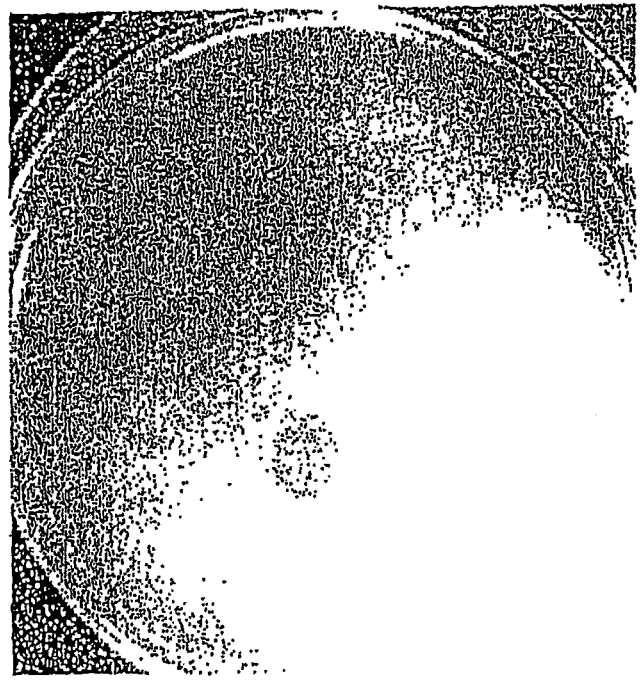
Ion discharge (15 min after)
(a)

Fig. 15

```
┌──────────────────────────────────┐
│  Preparing microorganism solution │
└──────────────────────────────────┘
              │
   ┌──────────┴──────────┐
   │                     │
┌─────────────┐    ┌──────────────┐
│  Spraying   │    │   Spraying   │
│(particle    │    │(no particle  │
│ release)    │    │  release)    │
└─────────────┘    └──────────────┘
       │                  │
┌─────────────┐    ┌──────────────┐
│  Sampling   │    │   Sampling   │
└─────────────┘    └──────────────┘
       │                  │
┌─────────────────┐ ┌─────────────────┐
│  Evaluation     │ │  Evaluation     │
│  *Plaque method │ │  * Plaque method│
│  *Hemagglutin.  │ │  * Hemagglutin. │
└─────────────────┘ └─────────────────┘
       │                  │
       └────────┬─────────┘
          ┌───────────┐
          │Comparison │
          └───────────┘
```

*Dependency on Irradiation Time

*Dependency on Particle Concentration

METHOD OF EVALUATING ELIMINATION OF MICROOGANISMS AND APPARATUS FOR EVALUATING ELIMINATION OF MICROORGANISMS

The present application is a Continuation of U.S. patent application Ser. No. 10/510,210, filed on Nov. 17, 2006, which is the National phase of PCT International Application No. PCT/IB/03/01250 filed on Apr. 7, 2003. This application also claims priority to Patent Application Nos. 2002-104306 filed on Apr. 5, 2002, 2002-326078 filed Nov. 8, 2002 and 2003-102054 filed Apr. 4, 2003 in Japan. All of the above applications' are hereby expressly incorporated by reference into the present application.

TECHNICAL FIELD

The present invention relates to a method for evaluating elimination of microorganisms so as to evaluate the sterilizing effect on microorganisms suspended in atmosphere and an apparatus for evaluating elimination of microorganisms.

BACKGROUND ART

Due to the highly airtight structure in living environment, a demand toward the elimination of microorganisms being suspended in air and hazardous for humans so as to have healthy and cozy life has increasingly grown. So as to satisfy the demand, filters with various antimicrobial agents attached thereon have been developed in recent years.

Because these filters are of a method to aspirate spatial air of space to filter off atmospheric microorganisms, however, these filters should essentially be maintained during long-term use, for example, by a filter exchange. Additionally, the performance of these filters is insufficient. Therefore, satisfactory performance has not yet been achieved. The method is insufficient as the method for eliminating microorganisms.

For generally carrying out the evaluation of eliminating suspended microorganisms, air containing microorganisms is passed through such filters to count the number of microorganisms filtered off. However, the concentration of microorganisms, which are subjected to be measured, suspended in air cannot be measured.

Meanwhile, as a method for eliminating microorganisms, there is a method of allowing particles such as ionized ions to irradiate microorganisms for a sterilizing treatment. However, it has not yet been carried out to measure and evaluate the performance of eliminating microorganisms with the sterilizing treatment of microorganisms utilizing the method.

It is therefore an object of the present invention to provide a method for evaluating elimination of microorganisms including allowing particles, particularly ion particles including positive ions and negative ions for the sterilizing treatment of microorganisms, particularly viruses to irradiate such microorganisms so as to evaluate the sterilizing effect, and an apparatus for evaluating elimination of microorganisms, which can be used for the method.

DISCLOSURE OF THE INVENTION

So as to solve the problems, the invention relates to a method for evaluating elimination of microorganisms comprising supplying microorganisms in the space inside a container, allowing particles with positive ions for a sterilizing treatment of microorganisms and particles with negative ions for a sterilizing treatment of microorganisms to simultaneously irradiate the microorganisms, and sampling the microorganisms and measuring the sampled microorganisms after the irradiation with the particles. Further, the invention relates to a method for evaluating elimination of viruses, comprising supplying viruses as microorganisms in the space inside a container, allowing particles for the sterilizing treatment of viruses to irradiate the microorganisms, sampling the viruses, and measuring the sampled microorganisms after the irradiation with the particles.

According to the method, microorganisms are sampled and measured after the irradiation of the particles in the space inside a container. Therefore, the performance of the irradiation of the particles for sterilizing treatment and elimination of microorganisms can be evaluated, so that various conditions for the irradiation of particles can be quantitatively evaluated.

Further, in the method for evaluating elimination of microorganisms, in addition to measuring microorganisms after the irradiation of the particles, under the same conditions for the sterilizing treatment of microorganisms with the irradiation of the particles, microorganisms can be supplied and be subjected to spontaneous decay without irradiation of the particles, and then the microorganisms can be sampled and measured.

In other words, according to the invention, in addition to doing the sterilizing treatment of microorganisms by the irradiation of particles for a given period of time, microorganism can be supplied under the same condition for doing the sterilizing treatment of microorganisms and microorganisms can be subjected to spontaneous decay for the same period of time as the given period of time for the irradiation of particles without irradiation of the particles and then microorganisms can be sampled and measured.

In such manner, microorganisms can be sampled and measured in both cases of the sterilizing treatment of microorganisms under the irradiation of particles and spontaneous decay of microorganisms without such sterilizing treatment. The results can be compared with each other. Thus, the sterilizing performance of the irradiation of particles can be relatively evaluated, compared with the case of the spontaneous decay of microorganisms.

Microorganisms can be measured by measuring the concentration of the microorganisms, the cell infection ratio, or the allergic reaction. In such manner, the evaluation for eliminating microorganisms can be conducted.

For measuring the sampled microorganisms, measuring the timewise change of the microorganisms can be measured in an irradiation time period of the particles, thereby making it possible to quantitatively evaluate the sterilizing performance over time.

For measuring the sampled microorganisms, the dependency of the elimination performance on the particles concentration can be measured, thereby making it possible to quantitatively evaluate the dependency of the sterilizing performance on the concentration of the particles.

For supplying microorganisms in the space inside a container, a solution of microorganisms in dispersion can be sprayed in a mist form. In such manner, microorganisms can be supplied easily in the inside of the container, thus leading to an easy sterilizing treatment. Additionally, the case where the microorganisms ares sprayed in a mist form can be a subject for the evaluation in accordance with the invention.

For the method for evaluation, cell culture using microorganisms, hemagglutination induced by microorganisms or allergic reaction induced by microorganisms can also be used. In such manner, the activity or concentration of the microorganisms can be evaluated.

As the particles for the sterilizing treatment of microorganisms, further, a gas generated by any of atmospheric electric discharge, atmospheric irradiation of radiation, and the Lenard effect can be used.

As the particles for the sterilizing treatment of microorganisms, furthermore, radiation, X ray, gamma ray or electromagnetic wave can be used. As the particles for the sterilizing treatment of microorganisms, still furthermore, positive ions and/or negative ions can be used.

It is now described below about the reason why sterilizing treatment using positive ions and negative ions as discriminating particles can be used for the sterilizing treatment of microorganisms.

When positive ions and negative ions are generated by triggering ionization phenomena such as electric discharge in atmosphere, $H^+(H_2O)n$ as a positive ion and $O_2^-(H_2O)n$ as a negative ion are generated in the most stable manner.

When these ions are generated, hydrogen peroxide $H_2O_2$ or radical OH as active species are generated by chemical reactions. Because the $H_2O_2$ or the radical OH has an extremely strong activity, microorganisms suspended in air can be subjected to sterilizing treatment and eliminated.

As the particles for the sterilizing treatment of microorganisms, further, a gas mainly containing positive ions or negative ions can be used. In that case, for example, an electric action due to the electric charge of the ions onto microorganisms causes cell damage or surface protein damage on the microorganisms, so that an effect of generating a sterilizing action can be given.

For the sterilizing treatment of microorganisms, additionally, a chemical agent in a particle form can be used for irradiation for the sterilizing treatment. For the sterilizing treatment using such chemical agent, the particle thereof can be supplied with a simple apparatus, compared with the cases due to ions or ozone. And, the sterilizing performance on such chemical agent can be evaluated.

The microorganisms as the subject for the sterilizing treatment may be a combination of one or more members selected from the group consisting of bacteria, mycete, viruses and allergens. In such manner, various microorganisms can be used as the subject for evaluating the elimination in accordance with the invention.

When supplying microorganisms in the space inside a container, the space inside the container can be stirred from a position below the supplied microorganisms. In such manner, for supplying microorganisms in the container, spontaneous settling of the microorganisms due to the weight of the microorganisms can be prevented, and the sterilizing treatment by irradiating particles can be carried out effectively. Further, the case where such stirring is conducted can also be a subject for the evaluation in accordance with the invention.

In accordance with the invention, further, an apparatus for carrying out the method for evaluating elimination of microorganisms can be provided, which includes a container for supplying microorganisms in the space inside the container and carrying out the sterilizing treatment of microorganisms therein, a microorganism supply means for supplying microorganisms in the space inside the container, a microorganisms elimination means for supplying particles for the sterilizing treatment of microorganisms in the space inside the container, and a microorganism sampling means for sampling the microorganisms after the sterilizing treatment due to the elimination of microorganisms means, and which works for measuring and evaluating microorganisms sampled by the microorganism sampling means.

According to the apparatus for evaluating elimination of microorganisms, the particles are irradiated by the microorganism elimination means for the sterilizing treatment, then, the microorganisms can be sampled by the microorganism sampling means and measured so as to evaluate the sterilizing performance of microorganisms by the microorganism elimination means on the basis of the measurement. And, various conditions for the sterilizing treatment of microorganisms by the irradiation of particles due to the microorganism elimination means can be evaluated quantitatively.

A specific embodiment of the apparatus for evaluating elimination of microorganisms can be constituted such that the microorganism supply means, the microorganism elimination means and the microorganism sampling means are sequentially arranged on the passage of air containing microorganisms, from the upstream side toward the downstream side thereof. In such manner, a series of processes comprising supplying microorganisms, elimination of microorganisms and sampling microorganisms can be carried out smoothly.

When a construction is selected such that a wind tunnel forming a passage of air containing microorganisms is interposed between the microorganism supply means and the microorganism sampling means, and the microorganism elimination means is arranged inside the wind tunnel in this case, the elimination, the sampling and the supply of the air containing microorganisms can be done in the limited wind tunnel.

Further, a construction is preferable such that the microorganism elimination means and the microorganism sampling means are arranged outside the vertically downward region of the microorganism supply means. Because particulate substances not prepared in a gaseous form in a mist discharged from the microorganism supply means fall in the vertically downward region and its peripheral regions, the microorganism elimination means and the microorganism sampling means are not contaminated with the fallen substances owing to such construction, so that the reliability of the evaluation apparatus can be improved. So as to attain the effect, importantly, the microorganism elimination means and the microorganism sampling means should not be arranged vertically downward the microorganism supply means. By arranging the microorganism supply means and the microorganism sampling means in the horizontal direction or by arranging both the microorganism elimination means and the microorganism sampling means in a position slightly shifted from the vertically downward position of the microorganism supply means or in a direction oblique to the direction of the microorganism supply means, for example, the effect can be gained.

In accordance with the invention, further, an apparatus for evaluating elimination of microorganisms can be used, where a separate container so as to cover the container is arranged outside the container. Due to such construction of the apparatus, microorganisms leaking from the container or particulate substances not prepared in a gaseous form can be shielded with the separate container, so that such microorganisms or such particulate substances hardly leak outside.

In the apparatus for evaluating elimination of microorganisms described above, a stirring means for stirring the space inside the container from a position below the supplied microorganisms can be arranged. In such manner, for supplying microorganisms from the microorganism supply means into the container, spontaneous settling of microorganisms due to their weight from the microorganism supply means can be prevented to effectively carry out the sterilizing treatment of microorganisms due to the microorganism elimination means.

The apparatus for evaluating elimination of microorganisms can be constituted such that the supply of microorganisms due to the microorganism supply means can be done by preparing a solution of microorganisms in dispersion in a mist form and then spraying the mist form in the space inside the container.

Additionally, the apparatus for evaluating elimination of microorganisms can be constituted such that the particles for the sterilizing treatment of microorganisms are discharged in the form of a gas generated by any of atmospheric electric discharge, atmospheric irradiation of radiation and the Lenard effect. Still additionally, the apparatus for evaluating elimination of microorganisms can have a construction such that the particles for the sterilizing treatment of microorganisms are in a form of radiation, X ray, gamma ray or electromagnetic wave and can be discharged in the apparatus.

Additionally, the apparatus for evaluating elimination of microorganisms can be constituted such that the microorganism elimination means can irradiate positive ions and/or negative ions as the particles for the sterilizing treatment of microorganisms. Still additionally, the apparatus for evaluating elimination of microorganisms can be constituted such that the microorganism elimination means can irradiate particles of chemicals as the particles for the sterilizing treatment of microorganisms.

BRIEF DESCRIPTION OF THE DRAWINGS

FIG. 5 shows a photograph obtained by photographing sampled microorganisms in Example 2, in which FIG. 5A is a photograph for microorganisms sampled in a case of conducting ion discharge and FIG. 5B is a photograph for microorganisms sampled in a case of not conducting ion discharge;

FIG. 15 is a flow chart for an evaluation test of Example 6;

BEST METHOD FOR CARRYING OUT THE INVENTION

Embodiments of the present invention are described below.

First Embodiment

Figure 1:
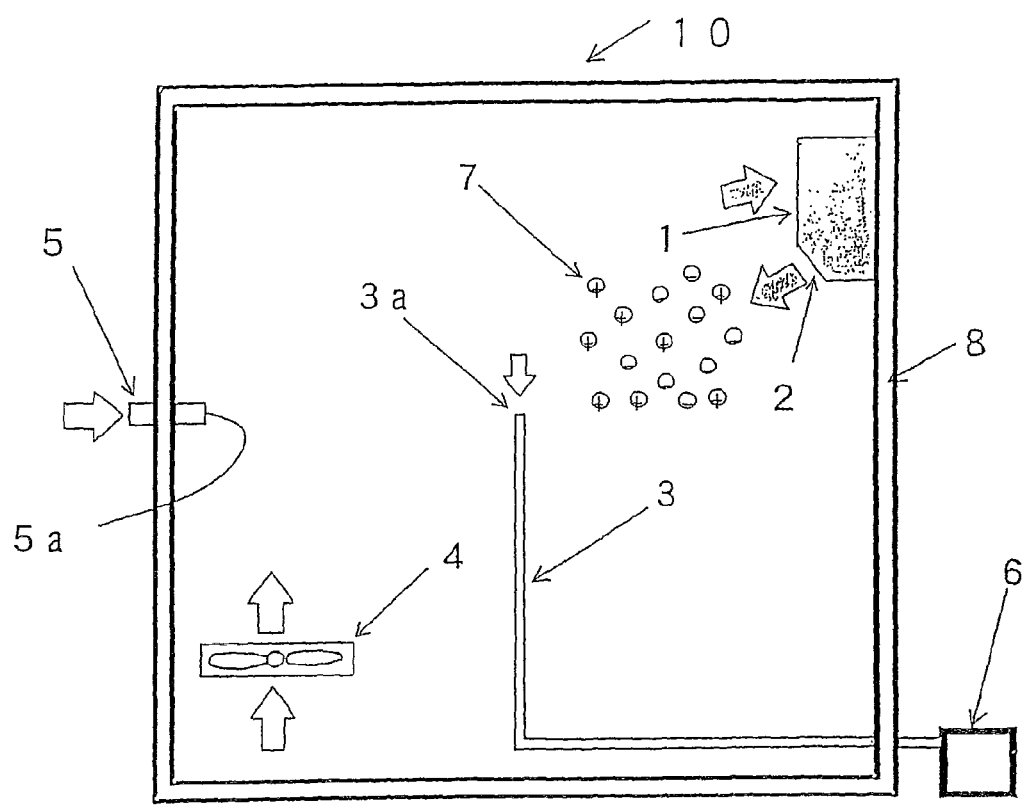
FIG. 1 is a schematic constitutional view showing a first embodiment of an apparatus for evaluating elimination of microorganisms according to the invention.

At first, an apparatus for evaluating elimination of microorganisms capable of carrying out a method of the invention is explained. FIG. 1 is a schematic constitutional view of an apparatus 10 for evaluating elimination of microorganisms as an example of an apparatus for evaluating elimination of microorganism. The apparatus 10 for evaluating elimination of microorganism comprises a container 8, a microorganism injection tube 5 constituting a microorganism supply means, an ion generation device 1 constituting a means for elimination of microorganisms, a microorganism sampling tube 3 and a microorganism sampler 6, both of which constitute a microorganism sampling means.

The container 8 has a structure with an inner space thereof being closed from an outside air and is adapted such that microorganisms are present in the space inside thereof and a sterilizing treatment for the microorganisms can be conducted.

Further, the temperature and the humidity in the inner space of the container 8 can be controlled optionally by an air conditioning system not illustrated particularly, so that environment can be set optionally for microorganisms.

Further, as shown in FIG. 1, the container 8 is formed such that the size in the direction of height is made larger than the size in the horizontal direction. Since this can take a larger volume for the space in the container 8, the treating capacity of the apparatus 10 for evaluating elimination of microorganism can be enlarged. The microorganism injection tube 5 is disposed at a predetermined position of the container 8 and can supply microorganisms by way of the microorganism injection tube 5 to the space inside the container 8, and microorganisms can be suspended in the space inside the container 8.

The microorganism injection tube 5 is adapted such that the microorganisms are sent from a microorganism supply source not particularly shown in FIG. 1. Then, microorganisms are injected into the container 8 from a microorganism injection port 5a facing the inside of the container 8.

For injection of the microorganisms from the microorganism injection tube 5 into the container 8, the microorganisms per se may be injected, or a solution in which the microorganisms are dispersed may be sprayed as a mist into the container 8.

The ion generation device 1 irradiates ions 7 as particles for the sterilizing treatment of microorganisms. The ion generation device 1 is disposed in the container 8 and irradiates the ions 7 from an ion generation port 2 to the microorganisms injected from the microorganism injection portion 5a into the container 8.

The ion generation device 1 has an ion generation element at the inside, and generates the ions 7 comprising positive ions and negative ions by ionization phenomena such as electric discharge or the like caused by the application of AC voltage between the electrodes of the ion generation element.

Generation of the ions 7 along with electric discharge or the like of the ion generation device 1 is not influenced in a state of air pressure in the container 8. Further, the intensity (concentration) of the ions 7 can be changed by controlling the operation voltage applied to the ion generation element of the ion generation device 1.

The microorganism sampling tube 3 for sampling the microorganisms is disposed in the space inside the container 8. As shown in FIG. 1, the sampling tube 3 comprises a portion disposed along a vertical direction which is a direction for the height of the container 8 and a portion disposed along the horizontal direction of the container 8.

The portion of the sampling tube 3 disposed along the horizontal direction extends to the outside of the container 8 passing through the lateral side of the container 8 and is connected with the microorganism sampler 6 to be described later at the outside of the container 8. A microorganism sampling port 3a is formed at the upper end in the vertical direction of the sampling tube 3, and the microorganisms in the container 8 are taken from the sampling port 3a into the sampling tube 3.

The microorganism sampler 6 is disposed outside the container 8 and constitutes, together with the sampler tube 3, a microorganism sampling means. The microorganism sampler 6 sucks the air in the space in the container 8 by way of the microorganism sampling tube 3 and takes the microorganisms in the container 8 from the microorganism sampling port 3a into the sampling tube 3 and also samples them to the microorganism sampler 6.

The microorganism sampler 6 for sampling the microorganisms can be constituted by using an air sampler. Further, the microorganism sampler 6 can also be constituted so as to sample the microorganisms through a solution bubbler.

As shown in FIG. 1, a stirrer 4 is disposed at the lower portion inside the container 8 in the apparatus 10 for evaluating elimination of microorganism. The stirrer 4 is a stirring means for starring the space in the container 8 and one adapted to form an air stream in the peripheral space by a rotating blower thereby stirring the space can be used.

When the stirrer 4 is disposed to stir the space in the container 8, it is possible to prevent microorganisms from spontaneous settling downward due to their weight and suspend microorganisms more effectively in a region where the ions 7 irradiated from the ion generation device 1 are present effectively.

Particularly, in a case where the microorganisms are of a heavy mass type, they tend to cause spontaneous settling but disposing of the stirrer 4 can prevent spontaneous settling and conduct the sterilizing treatment by the ions 7 effectively.

For carrying out the invention, it is not always necessary to provide the stirrer 4 but the sterilizing treatment by the ions 7 can be conducted effectively by disposing the stirrer with the reasons described above.

The method for evaluating elimination of microorganisms using the apparatus 10 for evaluating elimination of microorganisms can be conducted as described below. At first, a predetermined amount of microorganisms are injected from the microorganism injection port 5 into the container 8. Then, the ion generation device 1 is operated and the ions 7 are irradiated to the injected microorganisms to conduct a sterilizing treatment for the microorganisms. After irradiating the ions 7 for a predetermined period of time, the microorganisms are sampled by the microorganism sampler 6.

The number of cells can be measured for the sampled microorganisms. For measuring the number of cells of the microorganisms, this can also be conducted after culture of the sampled microorganisms on a predetermined culture medium in a culture medium petri dish for a predestined period of time. This can more accurately measure the number of cells of the sampled microorganisms. Further, the number of cells of the microorganisms can be measured by observing the microorganisms on the petri dish with a microscope.

As described above, by measuring the microorganisms sampled by the microorganism sampler 6 using the apparatus 10 for evaluating elimination of microorganism, the sterilizing performance to the microorganisms by the irradiation of the ion 7 can be evaluated.

Further, when elimination of the microorganisms is evaluated using the apparatus 10 for evaluating elimination of microorganism, the following measurement and evaluation can also be conducted. At first, as described above, after injecting a predetermined amount of microorganisms in the container 8, the ions 7 are irradiated to conduct the sterilizing treatment for a predetermined period of time and then the microorganisms are sampled by the microorganism sampler 6, and the number of cells of the sampled microorganisms is measured.

Then, the same amount of the microorganisms are injected into the container 8 under the same condition as that in a case of conducting the sterilizing treatment by irradiation of the ions 7. Then, after lapse of the same period of time as the time for irradiation of the ions 7, without irradiating the ions 7, the microorganisms are decayed spontaneously. Subsequently, the microorganisms are sampled by the microorganism sampler 6 and the number of cells of the sampled microorganisms is measured.

Then, the sterilizing performance by the ions 7 to the microorganisms can be evaluated relatively by comparison to the spontaneous decay, by comparing the number of cells of the microorganisms sampled after the sterilizing treatment by the irradiation of the ions 7 and the number of cells of the microorganisms sampled after the spontaneous decay.

Further, for the measurement of the microorganisms sampled by the microorganism sampler 6 as described above, the change with time for the number of cells of the microorganisms against the lapse of time from the start of the irradiation of the ions 7 or to the lapse of time after starting the spontaneous decay of microorganisms can also be measured.

Further, for the measurement of the microorganisms described above, measurement can be conducted for a case of conducting stirring and for a case of not conducting stirring by the stirrer 4.

Further, for the measurement of microorganisms, the intensity of the ions 7 to be irradiated to the microorganisms may be changed and measurement of the sampled microorganisms to each of the intensities of the ions 7 can also be conducted. Thus, the sterilizing performance to the microorganisms in accordance with the intensity of the ions 7 can be evaluated.

Second Embodiment

Figure 2:
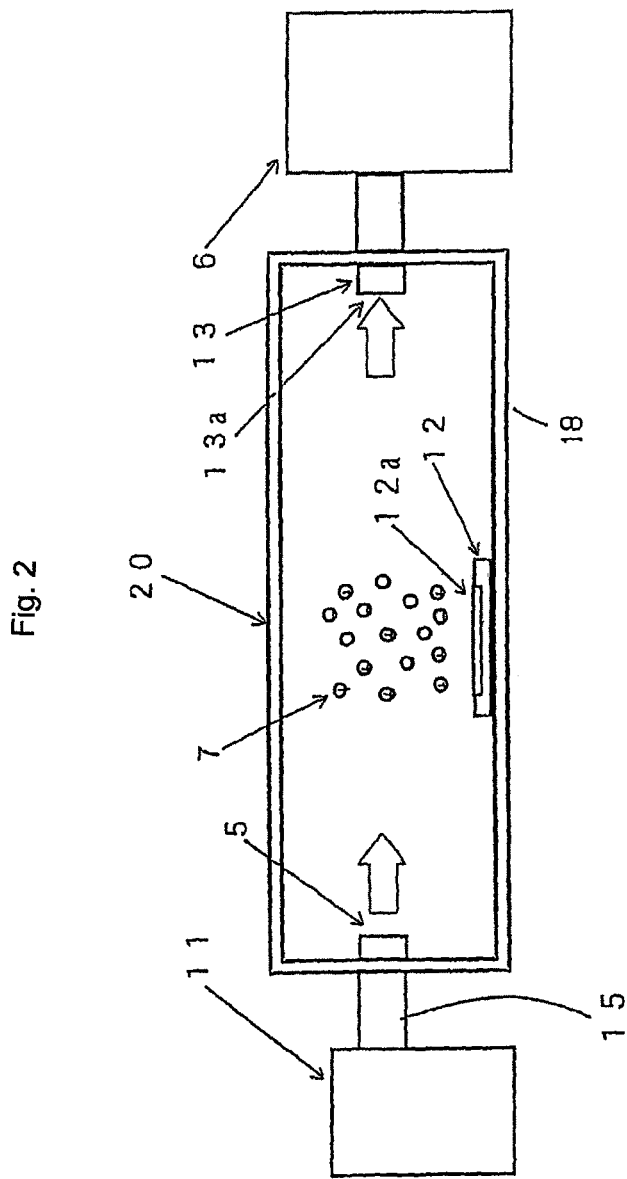
FIG. 2 is a schematic constitutional view showing a second embodiment of an apparatus for evaluating elimination of microorganisms according to the invention.

Then, a second embodiment of an apparatus for evaluating elimination of microorganism 20 is explained with referring to FIG. 2. FIG. 2 is a schematic constitutional view of the apparatus for evaluating elimination of microorganism 20 as the second embodiment of the apparatus for evaluating elimination of microorganisms.

The apparatus for evaluating elimination of microorganism 20 shown in FIG. 2 comprises a container 18, a microorganism injection tube 15 constituting a microorganism supply means, an ion generation element 12 constituting a microorganism eliminating means, a sampling tube 13 and a microorganism sampler 6 constituting a microorganism sampling means. That is, the microorganism injection tube 15 as the microorganism supply means, the ion generation element 12 as a microorganism elimination means, the sampling tube 13 and the microorganism sampler 6 as the microorganism sampling means are disposed sequentially from the upstream to the downstream in air passage containing microorganisms.

The container 18 has a structure with the inner space thereof being closed from the outside air and adapted such that microorganisms are present in the space inside thereof and the microorganisms can be sterilized. In the container 18, as can be seen from FIG. 2, the size in the direction of the height is made smaller compared with the size in the horizontal direction.

The microorganism injection tube 15 is connected to a microorganism sprayer 11 at the outside of the container 8, and the microorganisms are sent from the microorganism sprayer 11. The microorganism sprayer 11 sends a gas containing microorganisms at a predetermined concentration to the microorganism injection tube 15 at a constant velocity. Then, the gas containing the microorganisms sent from the microorganism sprayer 11 to the microorganism injection tube 15 is injected into the container 18 from a microorganism injection port 15a facing inside the container 18.

When the microorganisms are supplied from the microorganism sprayer 11 into the container 18, the microorganisms per se may be incorporated in air and sent to the microorganism injection tube 15, or they may also be sent into the microorganism injection tube 15 by spraying a solution in a mist form in which the microorganisms are dispersed.

The ion generation element 12 is disposed on the bottom surface in the container 18 outside the region vertically below the microorganism injection tube 15. The ion generation element 12 generates ions 7 comprising positive ions and negative ions by ion generation electrodes 12a which are arranged in a predetermined substantially planar-like configuration. Microorganisms injected from the microorganism injection tube 15 are sterilized by the ions 7 generated from the ion generation element 12.

The ion generation element 12 is the same as the ion generation element provided to the ion generation device 1 shown in FIG. 1 and the operation of generating the ions 7 is the same as that described for the ion generation device 1.

The microorganism sampling tube 13 for sampling the microorganisms is disposed along the horizontal direction outside the region vertically below the microorganism injection tube 15 and is formed at one end thereof with a microorganism sampling port 13a facing inside the container 18 and connected at the other end with the microorganism sampler 6 at the outside of the container 18.

The microorganism sampler 6 disposed at the outside of the container 18 sucks air from the space in the container 18 by way of the microorganism sampling tube 13, and takes the microorganisms in the container 18 through the microorganism sampling port 13a into the inside of the sampling tube 13 and samples them in the microorganism sampler 6. An air sampler can be used for the microorganism sampler 6 for sampling the microorganisms. Further, the microorganism sampler 6 can also be constituted to sample the microorganisms through a solution bubbler.

The method of the present invention can be carried out as described below by using the apparatus for evaluating elimination of microorganism 20. At first, a predetermined amount of microorganisms is injected from the microorganism injection port 15 into the container 18. Then, the ion generation element 12 is operated, the ions 7 are irradiated to the injected microorganisms to conduct the sterilizing treatment for the microorganisms. After irradiating the ions 7 for a predetermined period of time, the microorganisms are sampled by the microorganism sampler 6.

Then, the microorganisms sampled to the microorganism sampler 6 are measured. For measuring the sampled microorganisms, the number of cells for the sampled microorganisms can be measured. For measuring the number of cells of the microorganisms, it can also be conducted after cultivating the sampled microorganisms for a predetermined period of time on a predetermined culture medium with a culture medium petri dish. Further, measuring the number of cells of the microorganisms sampled can be conducted by observation using a microscope.

As described above, the sterilizing performance to the microorganisms by the irradiation of the ions 7 can be evaluated by measuring the microorganisms sampled in the microorganism sampler 6 by using the apparatus for evaluating elimination of microorganism 20.

Further, according to the apparatus for evaluating elimination of microorganism 20, a series of treatment including the injection of microorganisms by way of the microorganism injection port 15a into the container 18, the sterilizing treatment of the microorganisms by irradiating the ions 7 with the ion generation element 12 and subsequent sampling of the microorganisms by way of the microorganism sampling port 13a can be conducted substantially along one pass.

Therefore, according to the apparatus for evaluating elimination of microorganism 20, since it is not necessary to consider the spontaneous decay of the microorganisms in the container 18, evaluation for eliminating the aerial suspended microorganisms at high concentration can be conducted.

Further, according to the apparatus for evaluating elimination of microorganism 20, since the apparatus can be made compact and evaluation can be conducted in a closed space, even harmful microorganisms can also be evaluated.

Further, also in case of carrying out the method according to the present invention by using the apparatus for evaluating elimination of microorganism 20, the following measurement and evaluation can be conducted in the same manner as that explained for the case of carrying out the method by the apparatus 10 for evaluating elimination of microorganism shown in FIG. 1.

That is, the microorganisms sampled in the sampler 6 can be measured for the case of causing the microorganisms supplied into the container 18 to decay spontaneously without irradiation of the ions 7 and for the case of conducting the sterilizing treatment by irradiating the ions 7, and the results can be compared.

Further, when the sampled microorganisms are measured, it is also possible to measure the change with time for the number of cells of the microorganisms against the lapse of time after starting the irradiation of the ions 7 or lapse of time after starting the spontaneous decay of the microorganisms.

Further, the sterilizing performance to the microorganisms in accordance with the intensity of the ions 7 can be evaluated by changing the intensity of the ions 7 irradiated to the microorganisms and measuring the sampled microorganisms against each intensity of the ions 7.

In the above description, explanation has been made with the example of irradiating ions 7 comprising positive ions and negative ions as particles for the sterilizing treatment of the microorganisms.

Further, particles of chemicals may also be used as the particles for the sterilizing treatment of the microorganisms. In a case of using the particles of the chemicals, the present invention can be carried out by changing the ion generation device 1 of the apparatus 10 for evaluating elimination of microorganism shown in FIG. 1 or the ion generation element 12 of the microbial eliminating apparatus 20 shown in FIG. 2 to a means for spraying particles of the chemicals. In a case of using the particles of the chemicals, alcohol or aldehyde type chemicals, anti-viruses drugs or insecticides can be used as the chemicals.

Third Embodiment

Figure 8:
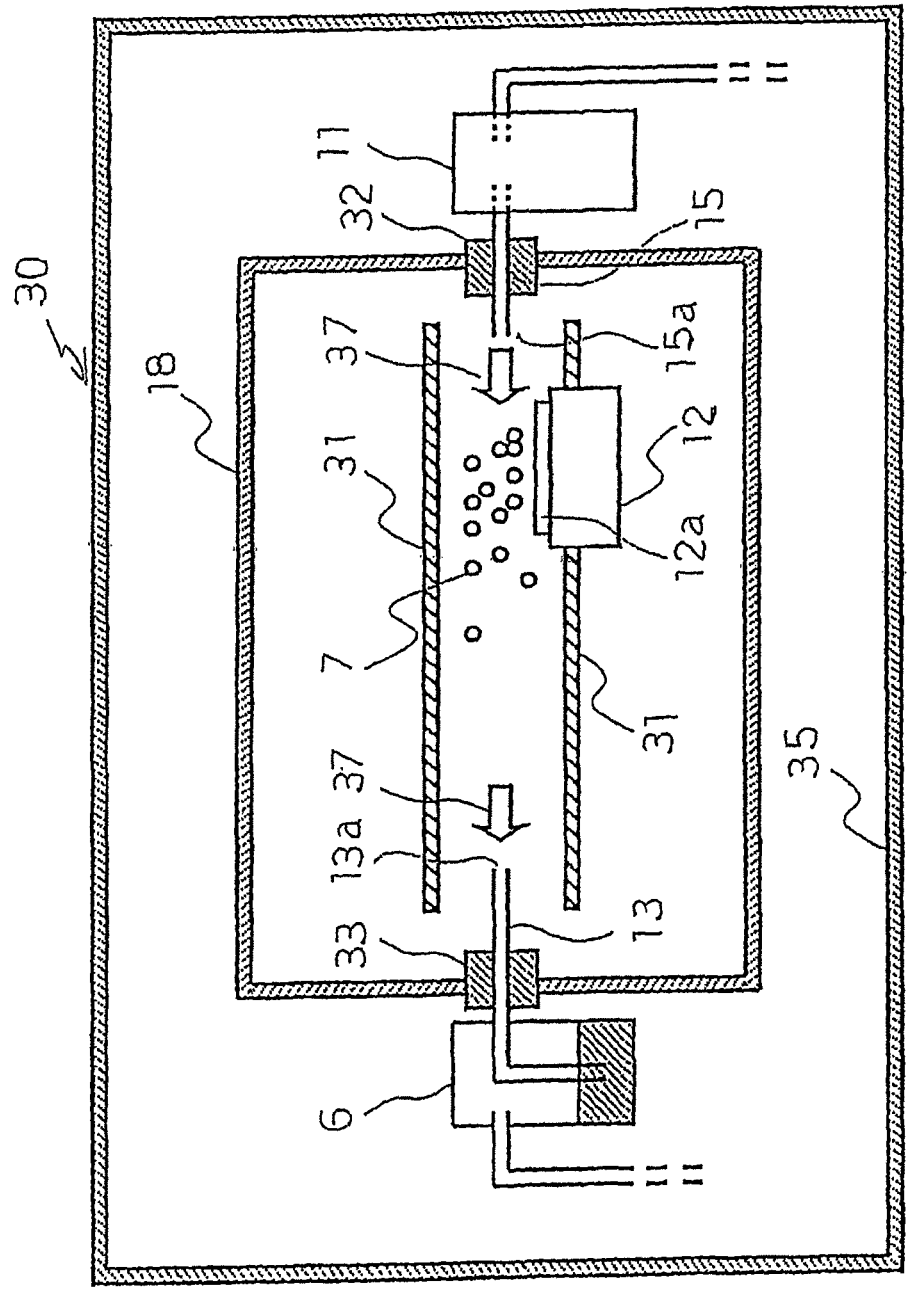
FIG. 8 is a schematic constitutional view showing a third embodiment and Example 6 of an apparatus for evaluating elimination of microorganisms.

Then, a third embodiment of the apparatus for evaluating elimination of microorganism according to the present invention will be described with reference to FIG. 8. FIG. 8 is a schematic constitutional view showing the third embodiment of an apparatus for evaluating elimination of microorganism. In comparison with the second embodiment, FIG. 8 has a feature in providing a wind tunnel and a separate container further at the outside of the container for sealing the inside.

That is, an apparatus 30 for evaluating elimination of microorganism of this embodiment comprises, as shown in the drawing, a container 18, a microorganism injection tube 15 constituting a microorganism supply means, an ion generation element 12 constituting a elimination of microorganisms means, and a sampling tube 13 and a microorganism sampler 6 constituting a microorganism sampling means. A wind tunnel 31 is disposed in a space from the injection tube 15 to the sampling tube 13 inside the container 18, and the ion generation device 12 is disposed in the wind tunnel 31.

The container 18 has a structure with an inner space thereof being closed from the outside air and formed such that the size in the height direction is made smaller compared with the size in the horizontal direction. On one side wall of the container 18, the injection tube 15 is extended by way of a seal packing 32 from the outside into the container, and the sampling tube 13 is extended by way of a seal packing 33 into the container on the opposite side wall opposed to the injection tube 15.

The microorganism injection tube 15 is connected at the outside of the container 18 with a microorganism sprayer 11 and microorganisms are sent through the microorganism sprayer 11. The microorganism sprayer 11 sends a gas containing microorganisms at a constant concentration to the microorganism injection tube 15 at a constant velocity. Then, the gas containing the microorganisms sent from the microorganism sprayer 11 to the microorganism injection tube 15 is injected into the container 18 from a microorganism injection port 15a facing the inside of the container 18. In this case, the microorganisms per se may be incorporated in air and sent into the microorganism injection tube 15, or a solution in which the microorganisms are dispersed may be sent by being sprayed in a mist form to the microorganism injection tube 15.

The wind tunnel 31 in the container 18 is formed cylindrically, disposed substantially horizontally and positioned such that the injection tube 15 and the sampling tube 13 are faced to both ends thereof.

The ion generation element 12 is disposed at the bottom surface in the wind tunnel 31 slightly upstream thereof, out of the region vertically below the microorganism injection tube 15. The ion generation element 12 generates positive ions and negative ions from ion generation electrodes arranged at a predetermined substantially planar configuration and sterilizes microorganisms injected from the microorganism injection tube 15.

The ion generation element 12 is the same as the ion generation element provided to the ion generation device 1 shown in FIG. 1 and the operation of generating the ions 7 is the same as that explained for the ion generation device 1.

The microorganism sampling tube 13 is disposed in the horizontal direction opposed to the microorganism injection tube 15, and a microorganism sampling port 13a facing the inside of the container 18 is formed at one end of the microorganism sampling tube 13, and the other end of the microorganism sampling tube 13 is connected to the microorganism sampler 6 at the outside of the container 18.

The microorganism sampler 6 accommodates bubbling liquid in it, and is constituted to collect microorganisms after taking in air sampled from the end of the microorganism sampling tube 13 submerged in the bubbling liquid and bubbling the air. Then, the entire spray test system including the container 18, the microorganism sprayer 11 and the sampler 6 is covered with a separate container 35.

In this embodiment, the mist emitted from the injection port 15a is sprayed inside the wind tunnel 31, and a slight gap is disposed between the injection port 15a and the wind tunnel 31 so as to drop unnecessary water droplets to the container 18.

Further, the gas emitted from the injection port 15a has a predetermined constant velocity by being sprayed and passes through the wind tunnel 31 in the direction shown by an arrow 37 in FIG. 8 at that velocity. By the mechanisms described above, particles comprising the ions discharged from the discharging electrodes of the ion generation element 12 affect the microorganisms, and the effect of eliminating the microorganisms by the ions till they reach the sampler 6 can be confirmed. The method for evaluating the microorganisms are not particularly limited and any evaluation method can be adopted such as evaluation methods by agar culture, evaluation by cell culture, hemagglutination, allergy reaction to living bodies or cells, or microscopic observation.

Further, since ingredients of the mist containing microorganism that are not vaporized but formed into water droplets dropping rapidly, and not-sampled microorganism ingredients are accumulated in the wind tunnel 31, the container 18 containing the same inside is constituted such that they are less leaked outside. Further, since the outside thereof is further covered with a separate container 35, it is not likely to affect persons or thr like at the outside. Accordingly, even when the wind tunnel 31 and the container 18 are not completely sealed containers, a probability of causing accidents such as biohazard can be decreased greatly. Further, since interfusion of unnecessary contaminants from the outside into the container 18 can be prevented by the shielding effect of the separate container 35, an effect which can improve the evaluation accuracy can be obtained.

Fourth Embodiment

Figure 9:
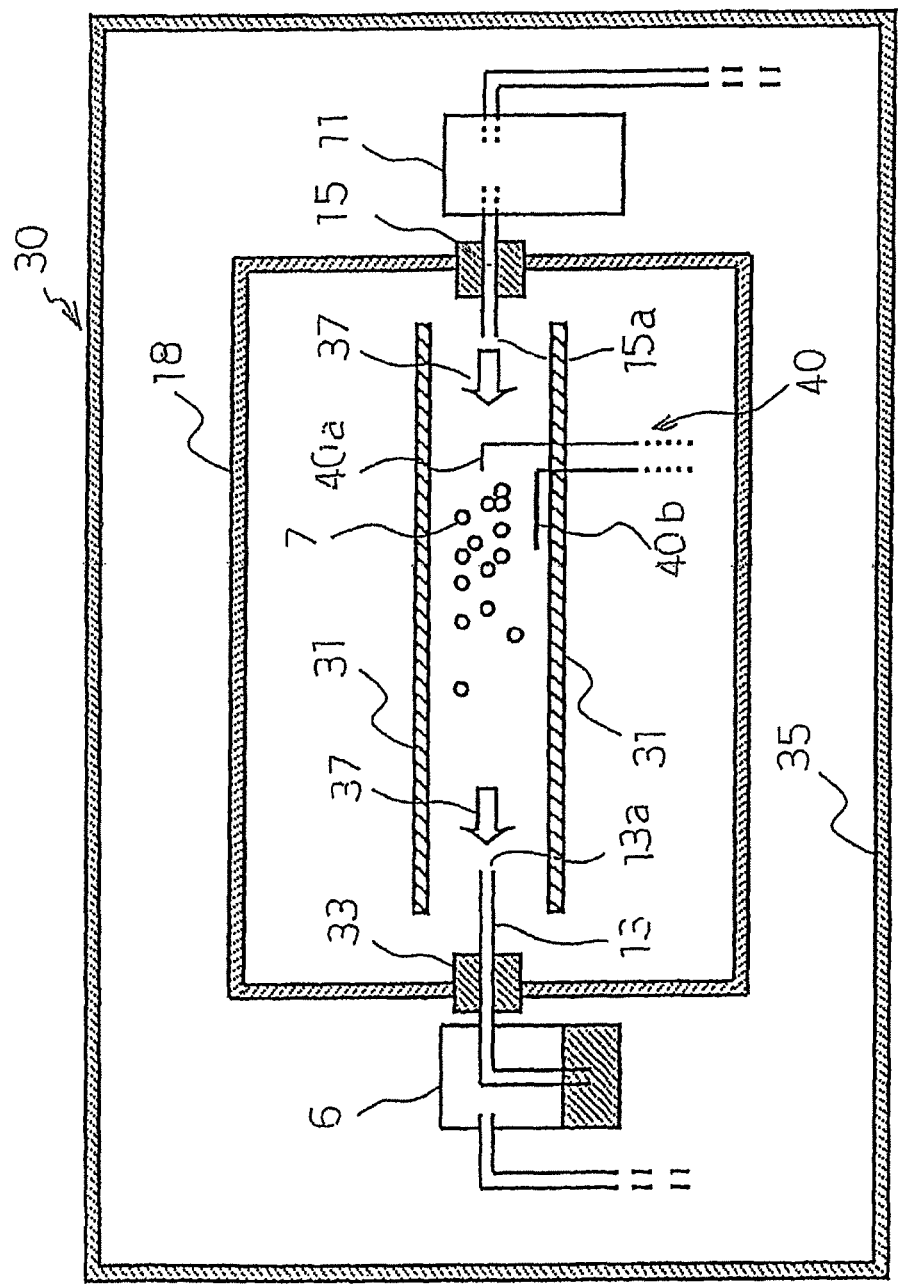
FIG. 9 is a schematic constitutional view showing a fourth embodiment of an apparatus for evaluating elimination of suspended microorganisms.
Figure 10:
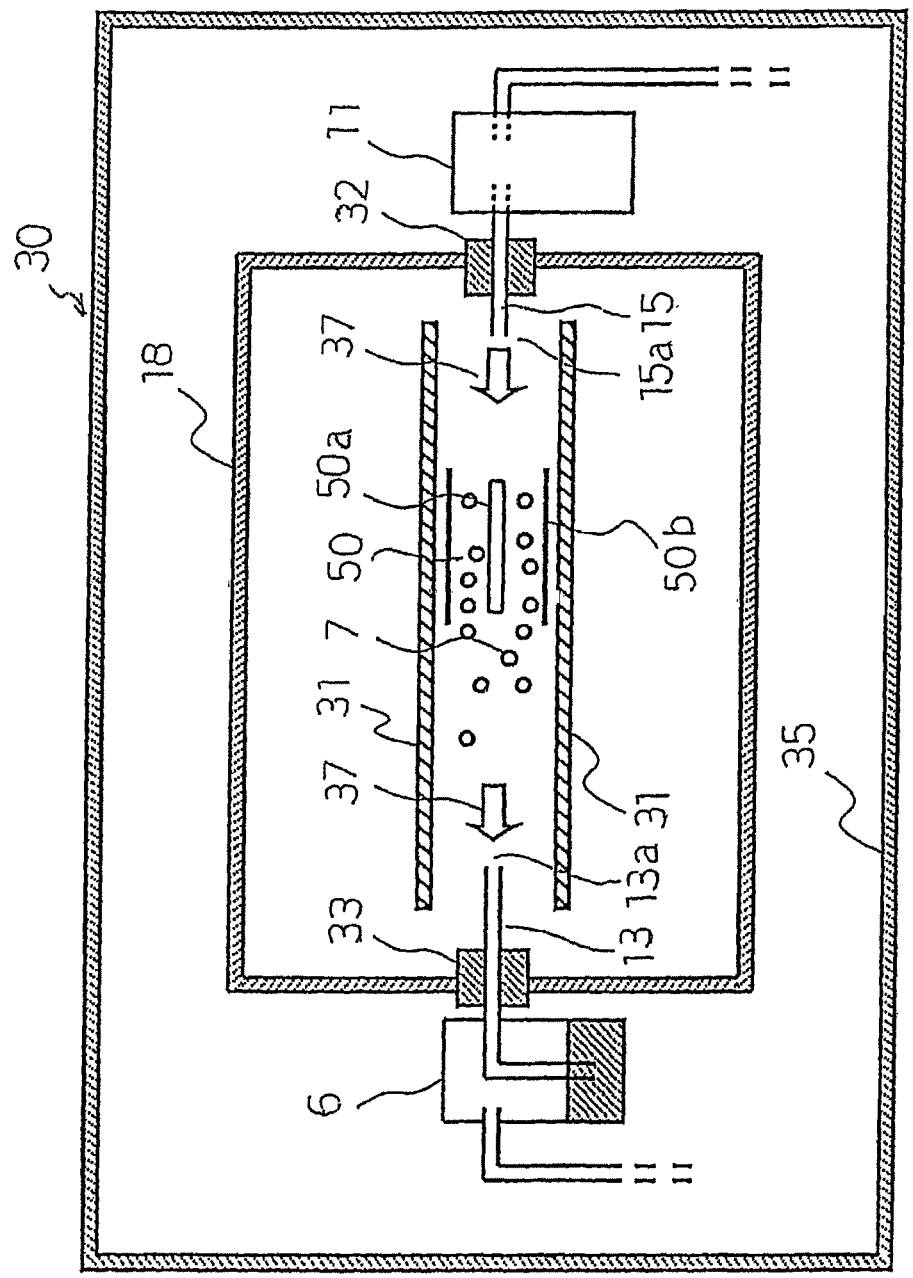
FIG. 10 is a schematic constitutional view showing a fifth embodiment of an apparatus for evaluating elimination of suspended viruses.

FIG. 9 is a schematic constitutional view of an apparatus for evaluating elimination of suspended microorganisms in which a particle emitting portion in the evaluation apparatus shown in the third embodiment is replaced with a needle-type electric discharge device 40.

That is, in this embodiment, a needle-like electric discharge device 40 is disposed instead of the ion generation element 12 in the third embodiment. The needle-like electric discharge device 40, disposed in the wind tunnel 31, comprises a needle-like electric discharge electrode 40a disposed in a upstream side region thereof and a counter plate electrode 40b disposed in opposition thereto. Since other constitutions are the same as those in the third embodiment, descriptions therefor are omitted.

In this embodiment, when a positive or negative high voltage at about several kv is applied to the needle-like electrode 40a, electric discharge occurs in the periphery of the top end of the needle and a gas mainly comprising ions charged positively or negatively as ionic ingredients are discharged.

According to the constitution described above, since the gas mainly comprising positive or negative ions are emitted and irradiated to a mist containing microorganisms discharged from the microorganism injection tube 15 and microorganisms are sterilized and eliminated, the evaluation test for eliminating microorganisms can be conducted.

In this embodiment, the discharged particles 7 are not limited only to the case mainly comprising ions but they may be radicals, ozone, active oxygen or other particles having sterilizing effect.

Fifth Embodiment

FIG. 10 is a schematic constitutional view of an apparatus for evaluating elimination of suspended viruses. In this embodiment, in the evaluating apparatus shown in the third embodiment, the particle emitting portion comprising the ion generation element 12 is replaced with a radical emitting mechanism comprising UV-lamps and catalysts.

That is, in this embodiment, a radical emitting mechanism 50 is disposed instead of the ion generation element 12 in the third embodiment.

The radical emitting mechanism 50, in the upstream side region in the wind tunnel 31, comprises UV-ray lamps 50*a* disposed substantially at the center portion and catalysts 50*b* oppositely disposed at the periphery of the UV-ray lamps 50*a*. Since other constitutions are identical with those in the third embodiment, descriptions therefor are to be omitted.

The catalyst 50*b* comprises a material containing, for example, platinum, gold or titanium oxide and has an operation such as applying energy of radiation light radiated from the UV-ray lamp 50*a* to radial formation and emitting the induced radials to the space.

The catalyst 50*b* is not limited only to the material containing platinum, gold, titanium oxide or the like but it will be apparent that those capable of emitting active gases can provide an evaluation test for elimination in the same manner.

Further, in this embodiment, the evaluation can be conducted also in the apparatus in which the catalyst 50*b* is removed. In this case, microorganisms present in the space can be sterilized by photon 7 as fine particles radiated from the UV-lamp 50*a*.

Further, this embodiment shows a case of generating radiation light from the lamp 50*a* and the radiation light having an energy from 5 eV to 20 eV is excellent in the sterilizing performance, and applying the radiation light including such light to this evaluation apparatus makes it possible to expect obtaining the evaluation result. Further, for the radiation light, a device of emitting X-rays or γ-rays may be disposed at a position for the UV-ray lamp 50*a* and the test can be conducted in the same manner.

The present evaluation method and apparatus for evaluating are effective in a way of usage to use them on the test for radioactive rays above described, but it will be apparent that other particles, for example, heat rays such as infrared rays, or visible rays may also be used, and they may be evaluated according to the present invention. In this case, it is considered, in principle, that thermal sterilizing performance is predominant and since intense thermal rays or visible light are required, it is desirable to separately dispose a heat dissipation mechanism or a light shielding plate.

Further, in case of using radioactive rays, sterilization with electromagnetic waves at 2 GHz to 200 GHz is available. In this case, the catalyst is not required particularly and the energy of the electromagnetic waves can be absorbed into the constituent elements of the microorganisms to destroy the microorganisms at the level of the molecules. The electromagnetic waves required for this purpose can include, for example, electromagnetic waves near 2.45 GHz, as a part of examples, which are considered to be easily absorbed in water. For example, electromagnetic waves from about 2 GHz to the shorter wave length region can be used.

At the frequency of equal to or higher than 2 GHz or higher, electromagnetic waves in a further higher frequency region that can be considered to be absorbed easily into elemental substances constituting microorganisms such as proteins can be a candidate, and it is considered that frequency up to 200 GHz is applicable to the sterilization as a possible frequency in the current situation of high frequency devices.

Further, in the apparatus shown in FIG. 10, an electromagnetic wave discharge device, optical waveguide device such as optical fiber or electric heater may be disposed at the position for the UV-ray lamp 50*a*.

(Microorganisms as Target)

The microorganisms as a target for the sterilizing treatment according to the present invention can include mycete, bacteria, viruses and allergenic substances inducing allergy (proteins, etc). In carrying out the invention, the mycete, bacteria, viruses and allergenic substance may be used alone or a plurality of them may be selected optionally and used in combination.

Since viruses generally belong to the region of the microorganisms, the effect of suppressing the growth thereof is expressed as the term of sterilization or elimination in the present invention. Generally, since the term of inactivation is often used for the effect of suppressing the growth of viruses, as for the viruses, the term of sterilization or elimination in the present specification may be used by replacing with the term of inactivation.

Further, in the same manner, also for the allergenic substance, the effect of suppressing the occurrence of allergic reaction for human bodies is expressed by the term of sterilization or elimination. Generally, since the effect described above can be replaced with the term of deactivation, the term of sterilization or elimination for the allergenic substance can be replaced with the term of deactivation in the present specification.

EXAMPLE

Example 1

Example 1 was practiced under the following conditions. For evaluating the elimination of microorganisms, an apparatus 10 for evaluating elimination of microorganism shown in FIG. 1 was used. The container 8 of the apparatus 10 for evaluating elimination of microorganism has a size for the inner space of 2.0 m length, 2.5 m width, and 2.7 in height.

Then, the atmosphere inside the container 8 was set to be a temperature of 25° C. and a relative humidity of 42%. Further, the space inside the container 8 was stirred by a stirrer 4. Stirring was conducted by the stirrer 4 at an air blow of 4 m$^3$/min.

*Escherichia coli* were used as microorganisms. The *Escherichia coli* were supplied into the container 8 in a mist form from a microorganism injection port 5a. Then, *Escherichia coli* were scattered at a concentration of about 500 to 1,500 N/m$^3$ in the container 8.

Further, a sampler 6 was constituted by using the Biotest Hyton RCS air sampler. The microorganisms were sampled at 40 liter/min for 4 min by the air sampler.

Then, ions 7 including positive ions and negative ions were irradiated by an ion generation device 1. In Example 1, the ion concentration was changed and the ions 7 were irradiated at each of the ion concentrations for 1 hour to conduct the sterilizing treatment. The ion concentration was expressed as values in the space at a distance of 10 cm from an ion discharge portion (ion generation port 2) of the ion generation device 1.

Then, after supplying *Escherichia coli* into the container 8 under the conditions described above, the ions 7 were irradiated at a constant ion concentration for one hour, and then *Escherichia coli* was sampled to the air sampler and the number of cells of the sampled *Escherichia coli* was measured. Then, the ion concentration of the ions 7 was changed and the measurement described above was repeated for each change of the ion concentrations.

FIG. 3 shows the result of measurement in Example 1. In FIG. 3, the abscissa corresponds to the ion concentration (N/$cm^3$) of the ions 7 in the logarithmic expression. Further, in FIG. 3, the ordinate corresponds to the suspended bacteria residual ratio (%). The suspended bacteria residual ratio represents the number of cells remained not sterilized after irradiation of the ions 7 by percentage.

From the result shown in FIG. 3, it was confirmed that the residual ratio of the aerial suspended bacteria was lowered when the concentration of the positive and negative ion emitted from the ion generation device 1 is increased. Further, it was also confirmed that the residual ratio of the aerial suspended bacteria is lowered rapidly when the negative or positive ion concentration is increased to 10,000 N/$cm^3$ or more.

Since the concentration of ions in usual rooms is from 500 to 1,500 N/$cm^3$, as a rough standard for providing the effect of eliminating the microorganisms effectively, it is considered appropriate to deliver the negative or positive ions at a concentration of 10,000 N/$cm^3$ or more.

Example 2

Example 2 was practiced under the following conditions. For evaluating the elimination microorganisms, the apparatus 10 for evaluating elimination of microorganism shown in FIG. 1 was used. The container 8 of the apparatus 10 for evaluating elimination of microorganism has a size for the inner space of 2.0 m length, 2.5 m width, and 2.7 m height.

Then, the atmosphere inside the container 8 was set to a temperature of 25° C. and a relative humidity of 42%. Further, the space inside the container 8 was stirred by the stirrer 4. Stirring was conducted by the stirrer 4 at an air flow of 4 $m^3$/min.

*Escherichia coli* were used as the microorganisms. The *Escherichia coli* in a mist were supplied into the container 8 via the microorganism injection port 5*a*. Then, *Escherichia coli* were scattered at a concentration of about 1,000 N/$m^3$ in the container 8.

Further, the sampler 6 was constituted by using the Biotest Hyton RCS air sampler. The microorganisms were sampled at 40 liter/min for 4 min by the air sampler. Then, sampling was conducted by the air sampler described above both in the case of delivering ions for irradiation of the ions 7 by the ion generation device 1 and in the case of spontaneous decay by delivering no ions for irradiation of the ions 7 by the ion generation device 1. In case of conducting the ion discharge, the ion concentration was set such that the negative and positive ions were each at 50,000 N/$cm^3$ in the space at a 10 cm distance from the ion discharge portion.

Then, *Escherichia coli* were sampled on every 15 min to the air sampler both in the case of conducting the ion discharge and the case of not conducting the ion discharge, and the number of cells of sampled *Escherichia coli* was measured.

FIG. 4 shows the result of measurement in Example 2, in which the change with time of the residual ratio of suspended bacteria (%) is shown. In FIG. 4, the abscissa corresponds to the lapse of time and the ordinate corresponds to the suspended bacteria residual ratio (%) in the same manner as in FIG. 3.

In the case of not conducting the ion discharge, the residual ratio of bacteria due to spontaneous decay after lapse of one hour was 80%. On the other hand, in the case of conducting the ion discharge, the bacteria residual ratio after lapse of one hour was 10%.

For the measurement described above, it is considered that difference of 10% against the residual ratio by spontaneous decay is a meaningful difference when the sampling accuracy of microorganisms and the concentration measurement accuracy is taken into consideration as the rough standard for judging the effect of eliminating microorganisms effective. Further, when the test accuracy is taken into consideration, in the case of not delivering ions, it is preferred to set such a test condition that the residual ratio of bacteria after lapse of one hour by spontaneous decay is 50% or more.

FIG. 5 shows a photograph taken for sampled *Escherichia coli* after lapse of 15 min both in the case of conducting ion release and the case of not conducting ion release. FIG. 5A is for the case of ion release and FIG. 5B is for the case of no ion release.

Further, when *Escherichia coli* shown in FIG. 5 were photographed, *Escherichia coli* sampled for each of the case were cultured on an agar medium at 34° C. and at 100% RH humidity for 48 hours and then photographed. Further, in FIG. 5, the size of the petri dish was 9 cm.

In the case of conducting the ion discharge, formation of *Escherichia coli* colony was not observed, as shown in FIG. 5A. On the other hand, in the case of not conducting the ion discharge, formation of *Escherichia coli* colony was observed, as shown in FIG. 5B. From the result shown in FIG. 5, it can be seen that the bacteria were eliminated by the ions.

Example 3

Example 3 was practiced under the following conditions. For evaluating the evaluation of microorganisms, the apparatus 10 for evaluating elimination of microorganism shown in FIG. 1 was used. The container 8 of the apparatus 10 for evaluating elimination of microorganisms has a size for the inner space of 2.0 m length, 2.5 m width and 2.7 m height. Then, the atmosphere inside the container 8 was set to a temperature of 25° C. and a relative humidity of 42%.

Further, in Example 3, comparison was made for the case of stirring and for the case of not stirring the inside of the container 8 which will be described later, and the stirring was conducted by the stirrer 4 at an air flow of 4 m$^3$/min in the case of stirring the space inside the container 8.

Cladosporium, a kind of mycete, were used as microorganisms. Cladosporium were supplied into the container 8 as a mist via the microorganism injection port 5a. Then, Cladosporium were scattered at a concentration of about 1,000 N/m$^3$ in the container 8.

Further, the sampler 6 was constituted by using the Biotest Hyton RCS air sampler. The microorganisms were sampled at 40 liter/min for 4 min by the air sampler.

Then, both in the case of conducting stirring by the stirrer 4 and the case of not conducting stifling by the stirrer 4, aerial suspended mycete were sampled by the air sampler on every 15 min and the number of sampled mycete was measured.

Figure 3:
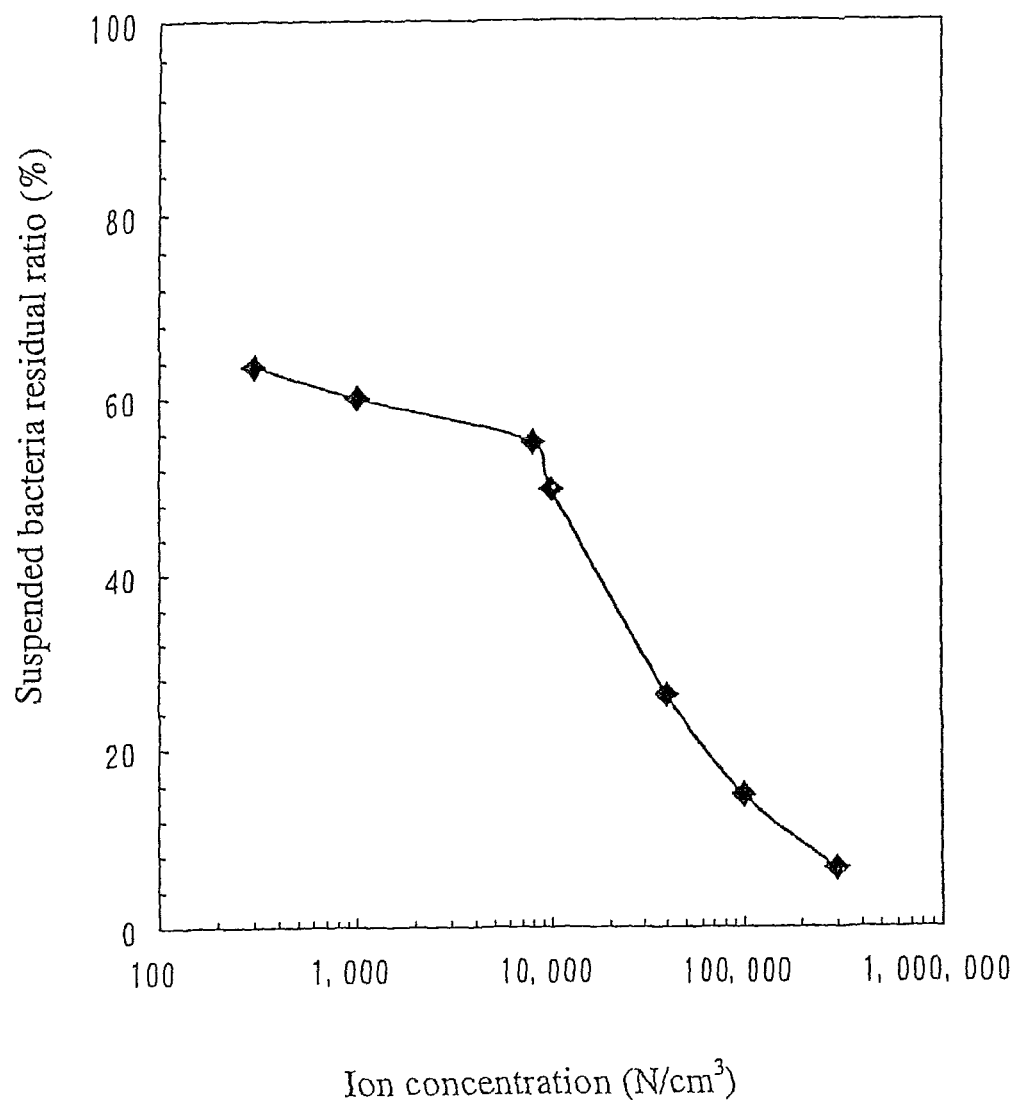
FIG. 3 shows the result of measurement for Example 1, which is a result of measurement for microorganisms sampled in a case of a sterilizing treatment while changing the ion concentration.
Figure 4:
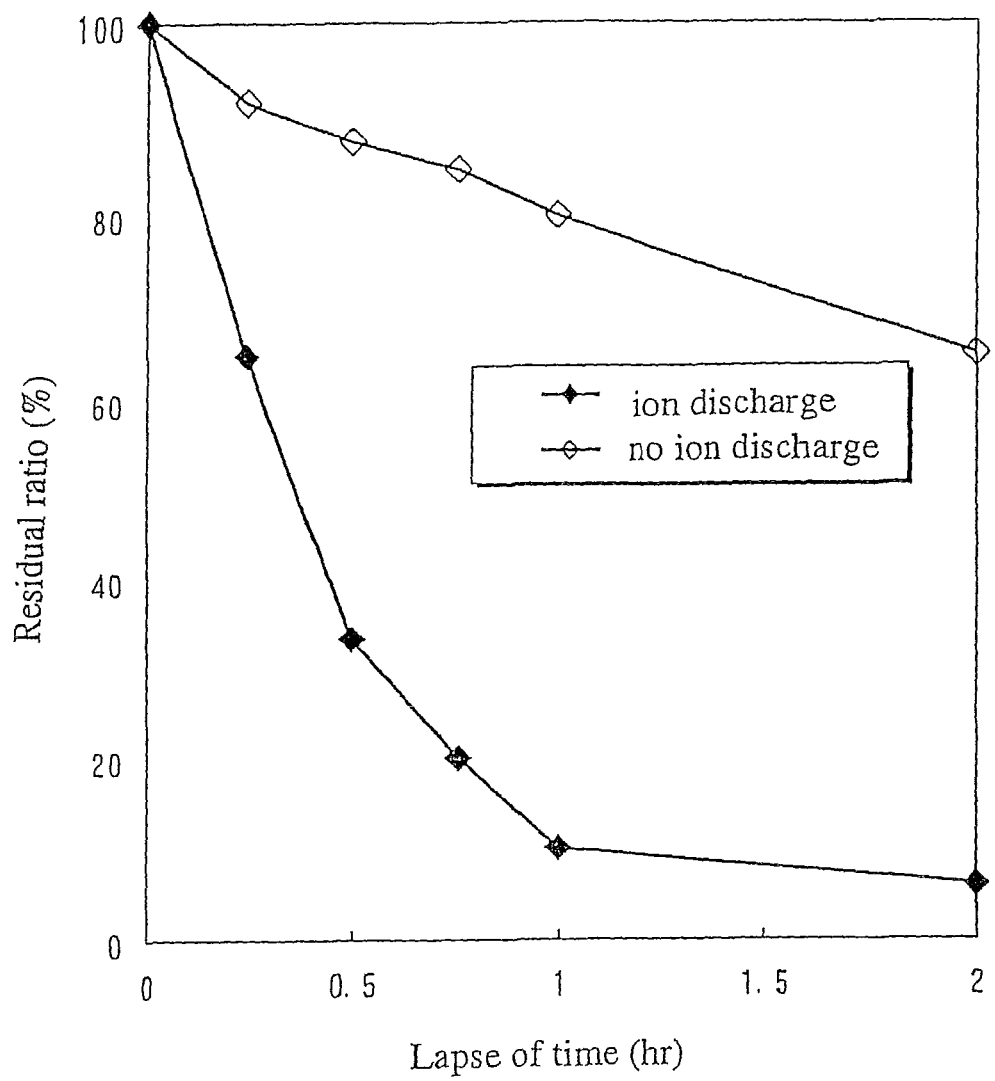
FIG. 4 shows the result of measurement for Example 2, which is a result of measurement for microorganisms sampled in a case of conducting ion discharge and in a case of not conducting ion discharge.
Figure 6:
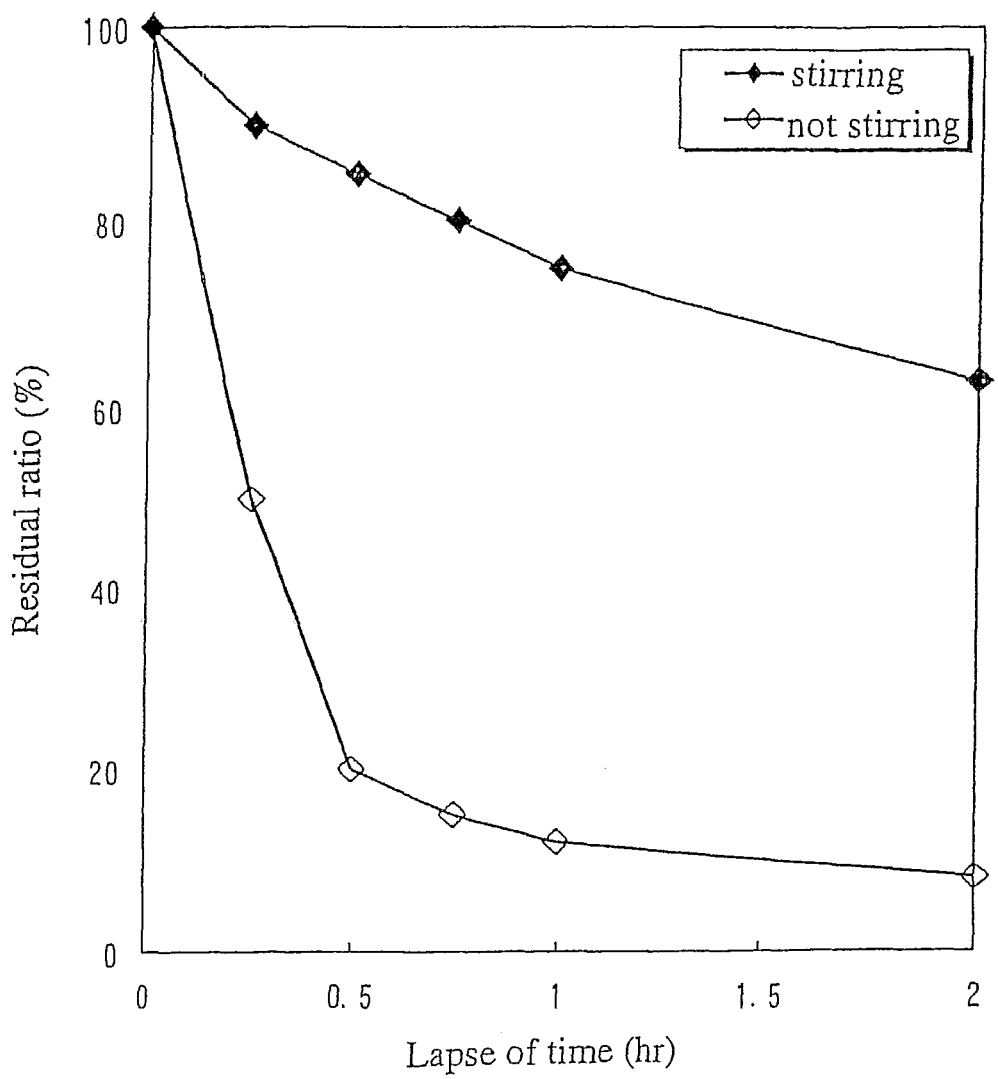
FIG. 6 shows the result of measurement for Example 3, which is a result of measurement for sampled microorganisms in a case of stirring and in a case of not stirring the inside of a container.

FIG. 6 shows the result of measurement in Example 3, in which the change with time of the residual ratio of aerial suspended mycete (%) by spontaneous decay depending on whether stirring was conducted or not is shown. In FIG. 6, the abscissa corresponds to the lapse of time and the ordinate corresponds to the suspended mycete residual ratio (%) in the same manner as in FIG. 3.

In the case of not conducting stifling, mycete reached a detection limit after lapse of 45 min and the residual ratio was 12%. On the other hand, in the case of conducting stirring, the residual ratio of mycete by spontaneous decay after lapse of one hour was 80%.

From the foregoing result, it can be said that stirring prevented mycete from falling spontaneously and facilitated evaluation of the suspended microorganisms. Particularly, stirring is effective in a case of mycete of large mass.

Example 4

Example 4 was practiced under the following conditions. For evaluating the elimination of microorganisms, the apparatus 10 for evaluating elimination of microorganism shown in FIG. 1 was used. The container 8 of the apparatus 10 for evaluating elimination of microorganism has a size for the inner space of 2.0 m length, 2.5 m width and 2.7 m height.

Then, the atmosphere inside the container 8 was set to a temperature of 25° C. and a relative humidity of 42%. Further, space in the container was stirred by the stirrer 4. Stirring was conducted by the stirrer 4 at an air flow of 4 m$^3$/min.

Cladosporium, a kind of mycete, were used as microorganisms. Cladosporium were supplied into the container 8 in a mist form via the microorganism injection port 5a. Then, Cladosporium were scattered at a concentration of about 1,000 N/m$^3$ in the container 8.

Further, the sampler 6 was constituted by using the Biotest Hyton RCS air sampler. The microorganisms were sampled at 40 liter/min for 4 min by the air sampler.

Then, mycete were sampled by the air sampler described above both in the case of delivering ions for irradiation of the ions 7 by the ion generation device 1 and the case of not delivering ions of spontaneous decay by delivering no ions for irradiation of the ions 7 by the ion generation device 1. In the case of conducting the ion discharge, the ion concentration was set such that the negative or positive ions were each at 50,000 N/cm$^3$ in the space at a 10 cm distance from the ion discharge portion.

Then, mycete were sampled on every 15 min to the air sampler for each of the case of conducting the ion discharge and the case of not conducting the ion discharge and the number of cells of sampled mycete was measured.

Figure 7:
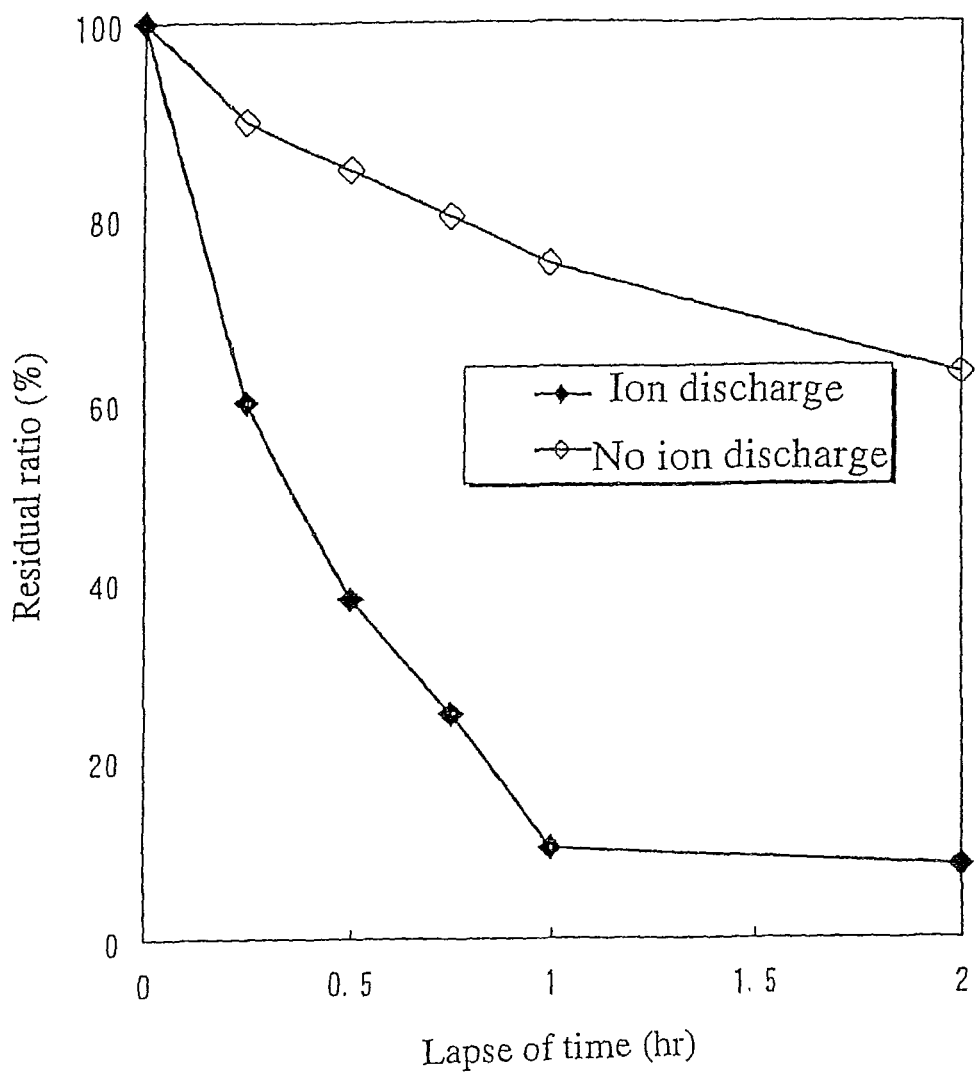
FIG. 7 shows the result of measurement for Example 4, which is a result of measurement for sampled microorganisms in a case of conducting ion discharge and in a case of not conducting ion discharge.

FIG. 7 shows the result of measurement in Example 4, in which the change with time of the residual ratio of suspended cells (%) is shown. In FIG. 7, the abscissa corresponds to the lapse of time and the ordinate corresponds to the suspended cell residual ratio (%) in the same manner as in FIG. 3.

In the case of not conducting the ion discharge, the residual ratio of cells due to spontaneous decay after lapse of one hour was 75%. On the other hand, in the case of conducting the ion discharge, the cell residual ratio after lapse of one hour was 10%.

For the measurement described above, it is considered that difference of 10% against the residual ratio by spontaneous decay is a meaningful difference when the sampling accuracy of microorganisms and the concentration measurement accuracy is taken into consideration as the rough standard for judging the effect of eliminating microorganisms effective. Further, when the test accuracy is taken into consideration, in the case of not delivering ions, it is preferred to set such a test condition that the residual ratio of cells after lapse of one hour by spontaneous decay is 50% or more.

Example 5

Example 5 was practiced under the following conditions. For evaluating elimination of microorganisms, the apparatus 20 for evaluating elimination of microorganism shown in FIG. 2 was used. The container 18 of the apparatus 20 for evaluating elimination of microorganism was formed to be a square pole shape of 8 cm square and 30 cm length. Then, the atmosphere inside the container 18 was set to a temperature of 28° C. and a relative humidity of 50%.

As microorganisms to be sterilized, polio viruses were used. An aqueous solution in which the polio viruses were dispersed by the number of several tens thousands per 1 cc was mixed with air to form a mist, which was supplied at a rate of 1 cc/min and at a blow rate of 1.6 m/sec from the injection port 15a into the container 18.

Further, in case of the sterilizing treatment by irradiation of the ions 7 to the polio viruses, the positive and negative ions were set each to 100,000 N/cm$^3$ in a space at a 10 cm distance from the ion discharge portion of the ion generation element 12.

Further, for sampling the polio viruses to the sampler 6 after the sterilizing treatment by the irritation of the ions 7, the viruses were separated and collected by a solution bubbler.

Then, when the polio viruses were sampled to the sampler 6 after the sterilizing treatment by the irradiation of the ions 7 and the number of cells was measured, the viruses elimination ratio was 78%.

Example 6

Figure 11:
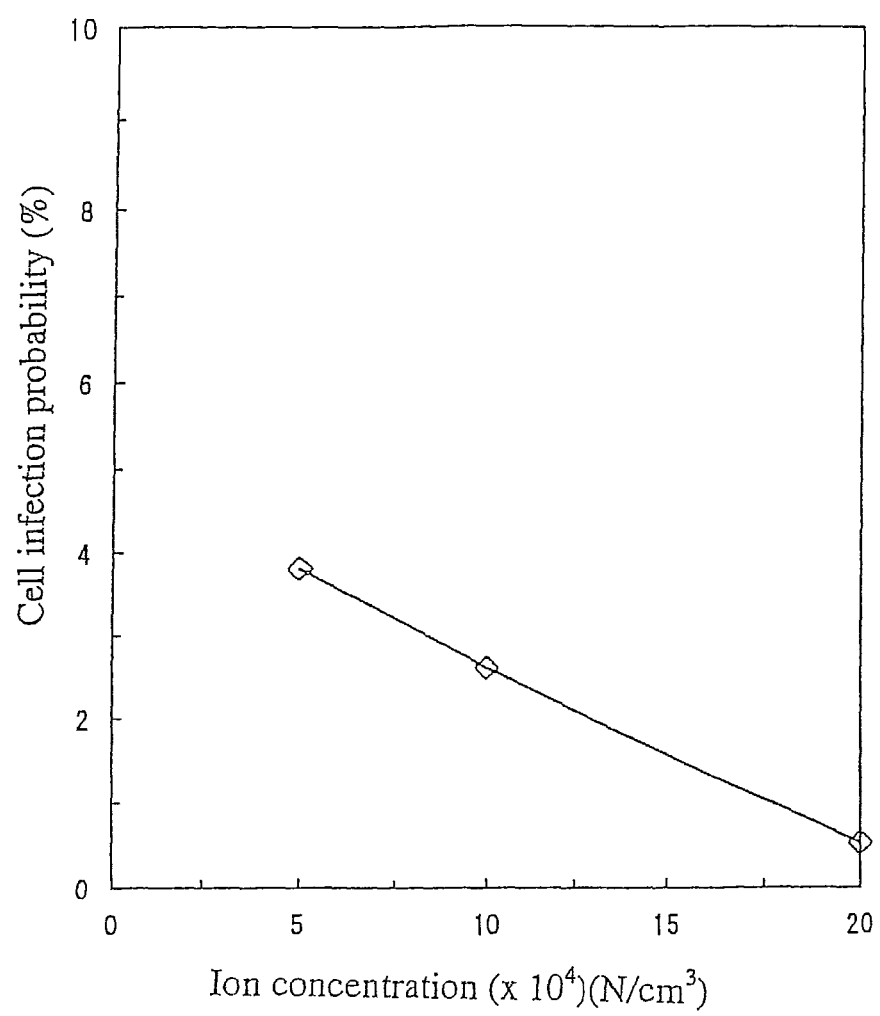
FIG. 11 is a graph showing a cell infection probability of influenza viruses depending on ion concentration of Example 6.
Figure 12:
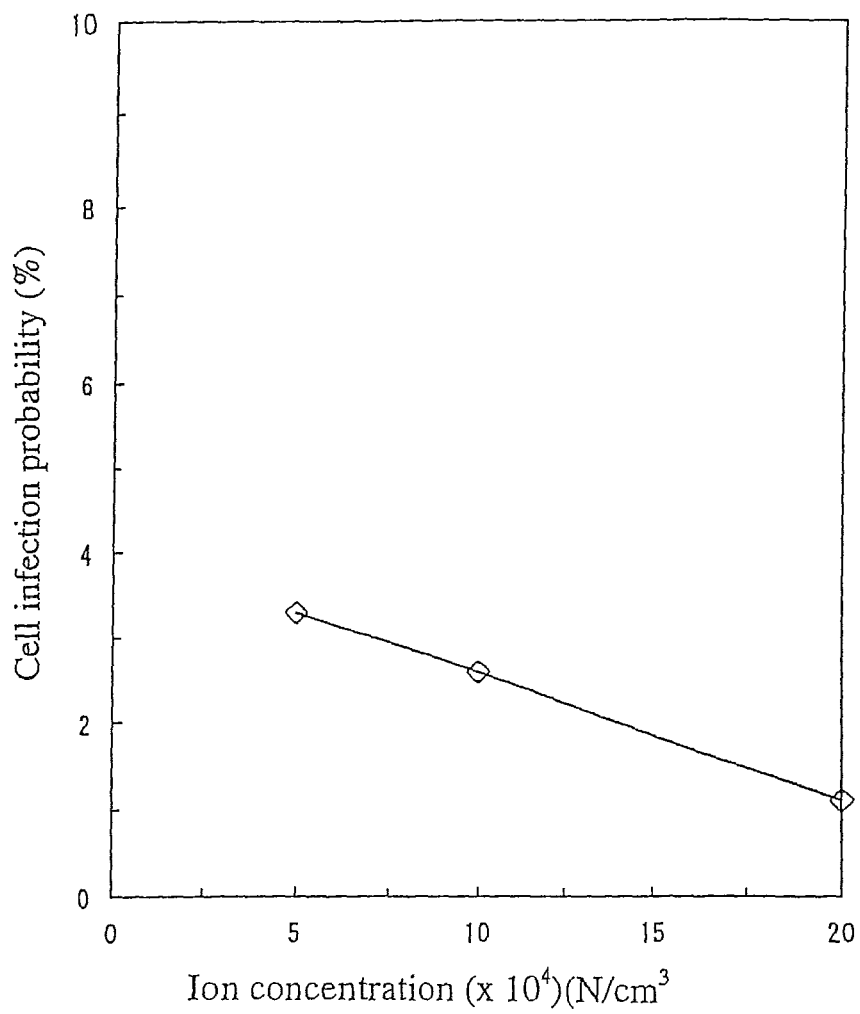
FIG. 12 is a graph showing a cell infection probability of Coxackie viruses depending on ion concentration of Example 6.
Figure 13:
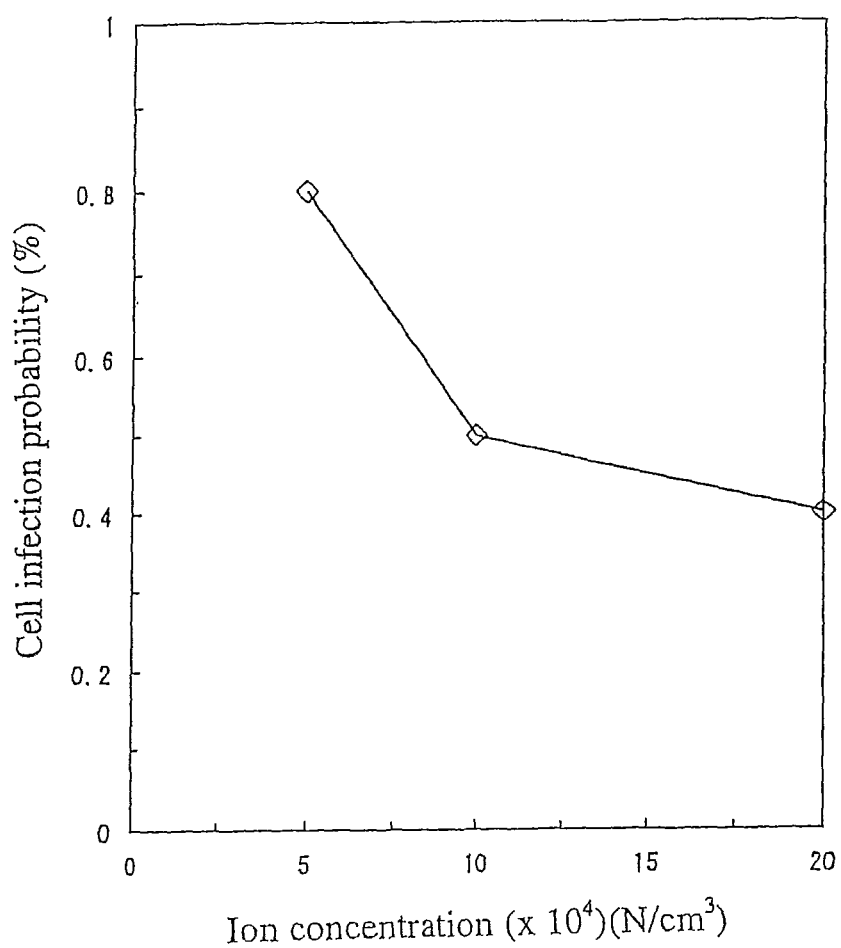
FIG. 13 is a graph showing a cell infection probability of polio viruses depending on ion concentration of Example 6.
Figure 14:
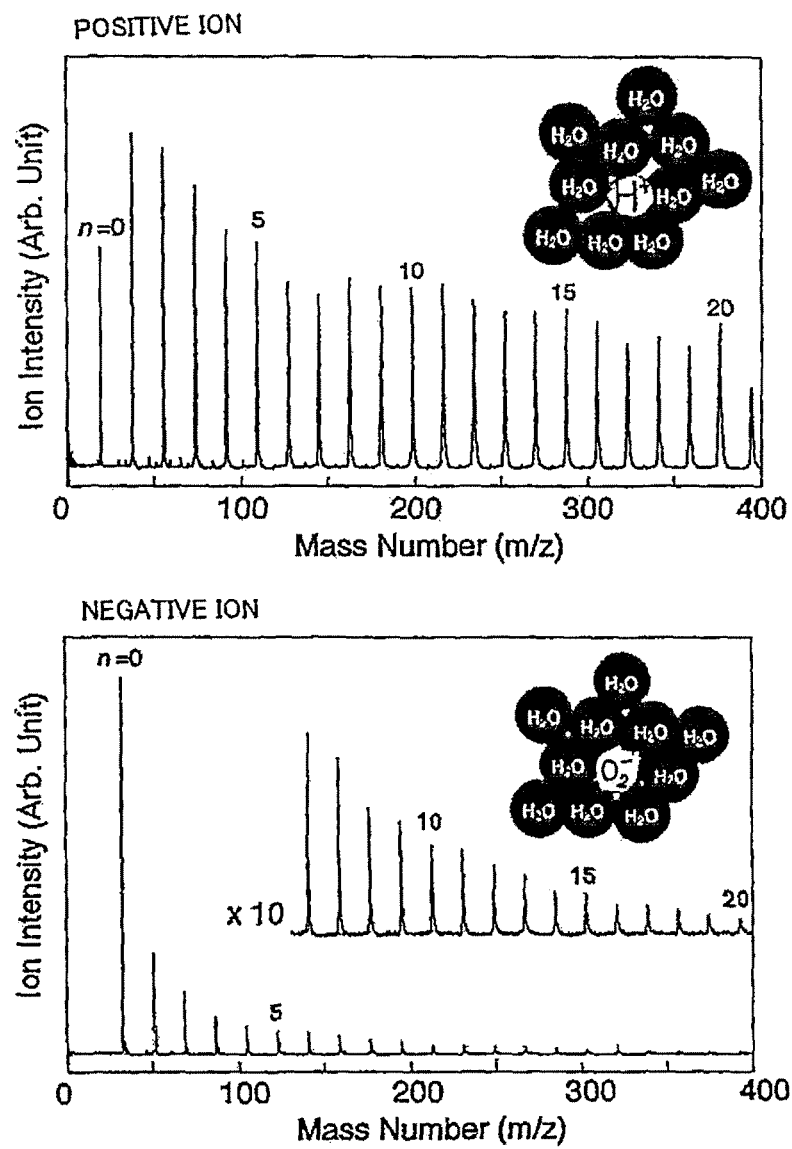
FIG. 14 is a graph showing mass spectrum for positive ions and negative ions formed from an ion generation element of Example 6.

Example 6 was practiced under the following conditions. FIG. 8 is a schematic constitutional view of an apparatus for evaluating elimination of suspended viruses of this example. FIG. 11 is a graph showing a cell infection probability of influenza viruses depending on the ion concentration, FIG. 12 is a graph showing a cell infection probability of Coxackie viruses depending on the ion concentration, and FIG. 13 is a graph showing a cell infection probability of polio viruses depending on the ion concentration. FIG. 14 is a graph showing mass spectrum for positive ions and negative ions formed from an ion generation element. FIG. 15 is a evaluation test flow chart for comparing the case of not operating the ion generation element with the case of operating the ion generation element. In the example, as shown in the flow chart of FIG. 15, after preparing a microorganism-containing solution, the solution was sprayed in a space by using a test apparatus and the air is sampled. A step of releasing and effectuating particles giving the sterilizing effect on the air containing the sprayed microorganisms is added after the spraying. The test was conducted for the case of releasing particles and the case of not releasing them. Using the solution sampled by the method described above, the concentration was measured or the activity of microorganisms was evaluated, for example, by means of the plaque method or hemagglutination. The effect of sterilizing treatment or inactivation is evaluated by comparing the case of acting with the case of not acting the particles, thereby enabling to make the effect of the particles distinct. By changing the concentration of the particles or the acting time of the particles, the dependency on the irradiation time or the dependency on the particle concentration can be examined regarding the extent of sterilization or inactivation.

In this example, the apparatus 30 for evaluating elimination of microorganism shown in FIG. 8 was used. The ion generation element 12 used in this case is a flat creeping discharge element of 37 mm length and 15 mm width. Creeping discharge was made to a surface electrode by alternately applying positive and negative high voltages between the electrodes, thus resulting in generating positive and negative ions by discharge plasmas at an atmospheric pressure.

The ion generation element 12 was attached and fixed to one end of an acrylic cylindrical container 31 of 55 mm inner diameter and 200 mm length. On one side of the container 18 for housing them, a viruses solution sprayer 11 is attached on one side and a sampler 6 for collecting viruses solution is attached on the other side thereof.

Influenza viruses were inoculated to a chorioallantois cavum of an embryonated egg and cultured in an incubator. Thereafter, a chorioallantois fluid was sampled as a test virus solution. The test virus solution was put in a glass atomizer (viruses solution sprayer 11) by 10 ml, and the glass atomizer was connected to one end of the container 18. A glass impinger (sampler 6) in which 10 ml of PBS(−) was incorporated was connected to the other end of the container 18. In the atomizer, a discharge pressure of pressurized air from an air compressor was controlled to be 0.48 hPa by a gauge pressure and the test viruses were sprayed from the injection port into the wind tunnel 31 in the container 18. The amount of spray was adjusted to 30 ml (spray flow rate 0.1 ml/min×spray time 30 min).

In this process, the ion generation concentration at 200,000 N/cm$^3$, 100,000 N/cm$^3$, and 50,000 N/cm$^3$ were compared with that in case of not operating the ion generation element 12 as a control.

The impinger sucked and collected the air in the test apparatus for 30 min at a suction flow rate of 10 L/min. PBS(−) obtained by sucking and collecting the air in the test apparatus via the impinger was used as a test solution, and influenza viruses were measured by the plaque method using MDCK cells. Further, Coxackie viruses and polio viruses were measured by the plaque method using Hela cells.

The plaque method is a sort of methods of injecting a viruseses-containing solution so as to be in contact with cells and confirming infection of viruses to the cells, and this is a method of examining the activity of the viruses, that is, the infection probability of viruses or the proliferation potential of viruses in the cells.

As for the ion concentration, an air blow was made to flow by a blower (not illustrated) at a blow rate of 4 mm/sec from one side of the cylindrical wind tunnel 31 in which the ion generation element 12 was disposed, an air ion counter manufactured by Dan Science Co. (Method No. 83-1001B) was disposed at a 10 cm distance from the ion generation element, and the ion concentration in the space was measured. The atmosphere in the space was set to a temperature of 25° C. and a relative humidity of 60% RH. Further, ion generation was confirmed in a range from a temperature of 0° C. and a relative humidity of 10% to a temperature of 40° C. and a relative humidity of 90%. The blower was used for confirming the ion concentration. In the actual evaluating of elimination of microorganisms, the blower was not used and air blow was caused by spraying from the sprayer 11 in the cylindrical wind tunnel 31.

As shown in FIG. 11, assuming the cell infection probability of the influenza viruses in a case of not operating the ion generation element is 100%, the cell infection probability was lowered greatly to 3.8%, 2.6%, and 0.5% in the case of generating ions by the number of 50,000, 100,000, and 200,000 (N/cm$^3$). Thus, it was confirmed that the eliminating performance for influenza viruses was improved by increasing the ion concentration.

Further, as shown in FIG. 12, assuming the cell infection probability of the Coxackie viruses in the case of not operating the ion generation element is 100%, the cell infection probability was lowered greatly to 3.3%, 2.6%, and 1.1% in the case of generating ions by the number of 50,000, 100,000 and 200,000 (N/cm$^3$). Thus, it was confirmed that the eliminating performance for Coxackie viruses was improved by increasing the ion concentration.

Further, as shown in FIG. 13, assuming the cell infection probability of the polio viruses in the case of not operating the ion generation element is 100%, the cell infection probability was lowered greatly to 1.0%, 0.5%, and 0.4% in the case of generating ions by the number of 50,000, 100,000 and 200,000 (N/cm$^3$), and it was confirmed that the eliminating performance for polio viruses was improved by increasing the ion concentration.

As shown in FIG. 14, the generated ions have a composition that positive ions ionize molecules of water in air by plasma discharge to form hydrogen ions $H^+$ and water molecules in air are clustered with hydrogen ions by the solvation energy, and that negative ions ionize molecules of oxygen or water molecules in air by plasma discharge to form oxygen ion $O_2^-$ and molecules of water in air are clustered with oxygen ions by the solvation energy.

Positive and negative ions delivered to the space surround viruses suspended in air, and positive and negative ions generate active species of hydrogen peroxide $H_2O_2$ or radical OH due to chemical reaction at the surface of viruses, thereby destroying and killing proteins. With the method as described above, viruses in air can be effectively sterilized and eliminated.

As a method of examining the activity of viruses, hemagglutination can also be used. The hemagglutination is a method of injecting a viruseses-containing solution, for example, into a solution containing a blood of chicken and observing blood coagulation. Presence of viruses can be confirmed by utilizing the phenomenon that hemagglutinin existing on the surface of viruses acts on plural red cells to induce coagulating of the blood cells.

Further, as a method of examining the concentration of the viruses, the concentration of active viruses, that is, the concentration of viruses having infectivity by the activation of the hemagglutinin can be examined relatively by diluting the viruses with aqueous solutions so as to obtain a plurality of concentrations and confirming whether each of the diluted solutions causes hemagglutination or not.

Example 7

Figure 16:
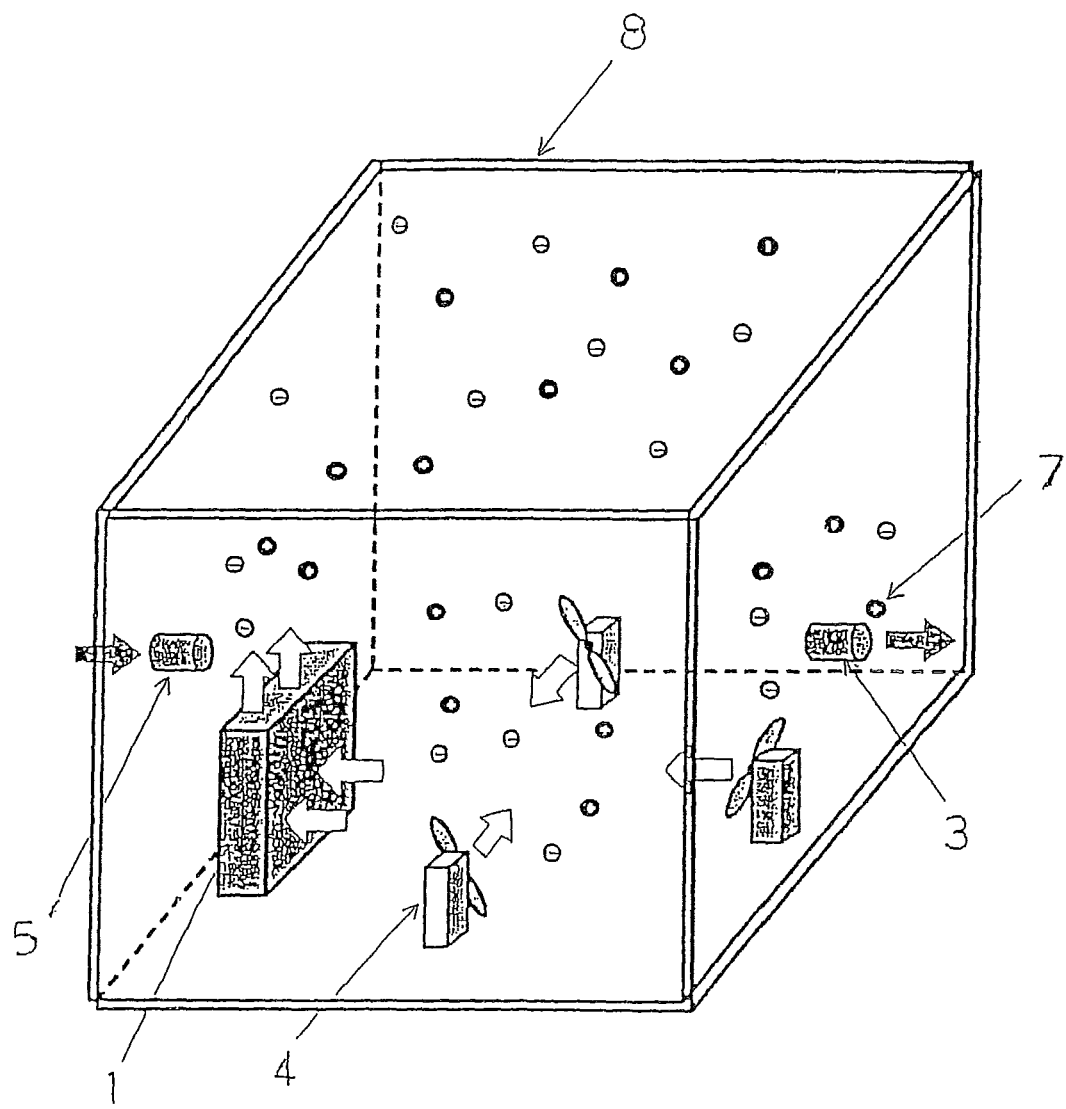
FIG. 16 is a schematic view of an apparatus for evaluating elimination of suspended pathogenic bacteria of Example 7.
Figure 17:
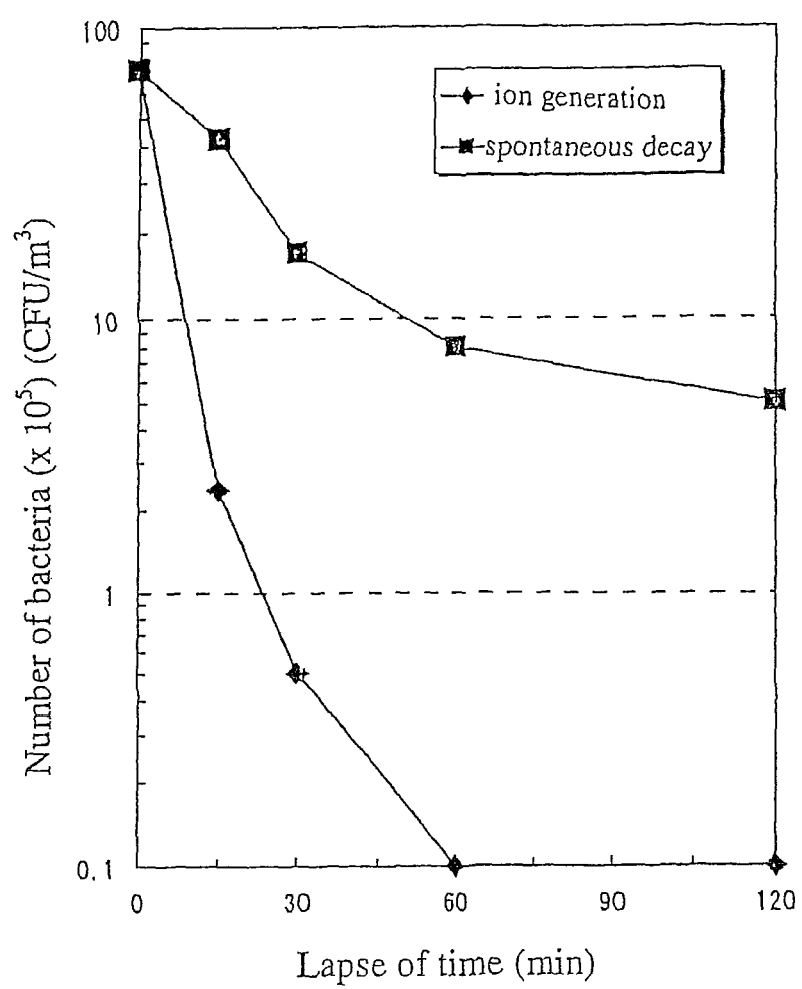
FIG. 17 is a graph showing the change with time of the concentration of aerial suspended Staphylococcus bacteria at the ion concentration of 200,000 N/cm$^3$ of Example 7.
Figure 18:
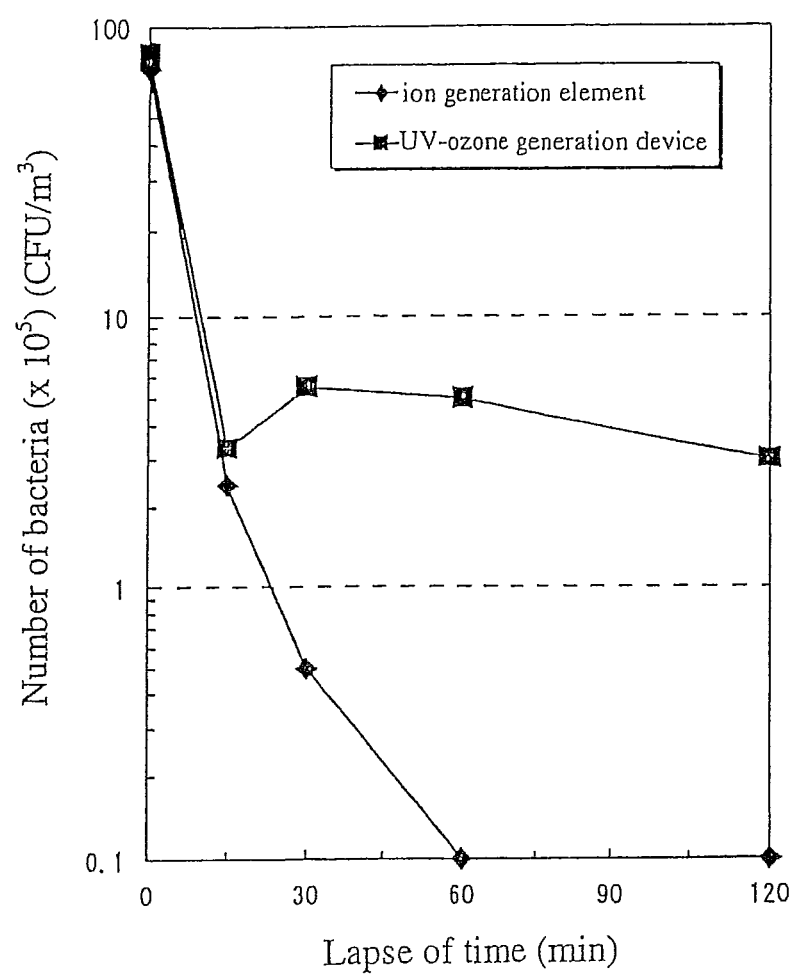
FIG. 18 is a graph showing the change with time of the concentration of aerial suspended Staphylococcus bacteria by an ion generation element and a UV-ray ozone generation device of Example 7.

FIG. 16 is a schematic view of an apparatus for evaluating elimination of a suspended pathogenic bacteria. FIG. 17 is a graph showing change with time of a concentration of aerial suspended Staphylococcus at an ion concentration of 200,000 N/cm$^3$. The same ion generation device as in Example 6 was used. FIG. 18 is a graph showing change with time of the concentration of aerial suspended Staphylococcus bacteria by an ion generation element and a UV-ray ozone generation device. The atmosphere in the space was at a temperature of 25° C. and at a relative humidity of 60% RH. The generation of ions was confirmed in a range from a temperature of 0° C. and a relative humidity of 10% to a temperature of 40° C. and a relative humidity of 90%.

For demonstrating the effect of eliminating suspended Staphylococcus bacteria existing in a predetermined space by the ion generation element, the way of testing substantially equal with that shown in FIG. 1 was used in this test. That is, the container 8 made of FRP, having acrylic plates attached on both ends thereof, with a space of 1 m$^3$ of 1 m×1 m×1 m size, was used. The ion generation element 1 was attached to a portion of an upper air blow port of a blower at a flow rate of 2 m$^3$/min in the container.

Further, for suspending the sprayed bacteria for a long time, axial flow blowers 4 each of 15 cm square were placed by four units at four corners of the container 8 such that the air blow was directed upward. The injection tube 5 for spraying bacteria solution was disposed at one end of the acrylic plate of the container 8, which was used as a test apparatus.

For the test bacteria, preserved strains were inoculated on a Trypticase Soy Agar medium (BBL) and cultured at 35° C. for 24 hours. The bacteria were diluted, and conditioned by sterilized physiological saline, washed and then used as test bacteria.

The test bacterial solution was charged by 10 ml to a glass atomizer, which was connected to one end of the test apparatus. A glass impinger incorporated with 100 ml of sterilized physiological saline was connected to the other end of the container 8. In the atomizer, the discharged pressure of pressurized air from an air compressor was controlled to be 0.48 hPa by a gauge pressure and the test bacteria were sprayed from a spray port. The amount of spray was adjusted to be 1.0 ml (spray flow rate 0.1 ml/min×spray time 10 min). The axial flow blower 4 was operated at the same time with the spraying of the bacteria solution and operated continuously to the end of the test.

At the instance the spray was completed, the air in the container 8 was sucked and collected by the impinger at a suction flow rate of 10 L/min for 10 min. This was defined as 0 min value. In the case of operating the ion generation element 1, the ion generation element and the blower were operated simultaneously. After starting the operation and lapse of a predetermined period of time, the air in the container was sucked and collected by 100 L in the same manner as that for 0 min value. The ion generation concentration was set to be 200,000 N/cm$^3$.

Further, also in the case of not operating the ion generation element (spontaneous decay value), it was operated in a state of operating only the blower 4 without operating the ion generation element, and the air in the container was sucked and collected on every lapse of time.

Further, for conducting a comparative experiment with ozone, a test was conducted by using a UV-ray ozone generation device (OZ51N-1, Sen Tokushu Kogen K.K.) at the same amount of the ozone generation amount of 1.637 mg/h (22° C., 17% RH) as the amount of ozone formed from the ion generation element.

A sterilized physiological saline formed by sucking and collecting air in the container by the impinger was used as a test solution, which was diluted stepwise by using sterilized physiological saline, and the stock solution and each of the diluted solutions were coated on the Trypticase Soy Agar medium (BBL) and cultured at 35° C. for 48 hours. After culturing, the number of colonies grown on the medium was counted and indicated by the number of cells per sucked air.

As shown in FIG. 17, compared with the case of not operating the ion generation element, it was confirmed that the concentration of the suspended bacteria after lapse of 30 min was decreased to about 1/10 when the ions were generated. Further, after lapse of 60 min, suspended bacteria were no more detected.

As shown in FIG. 18, compared with the case of UV-ray ozone generation device, it was confirmed that the concentration of suspended bacteria was decreased to about 1/10 after lapse of 60 min by the ion generation element. Accordingly, the sterilizing effect was confirmed by the effect described for Example 6 also for Staphylococcus bacteria which are typical bacteria causing hospital infection.

Example 8

Figure 19:
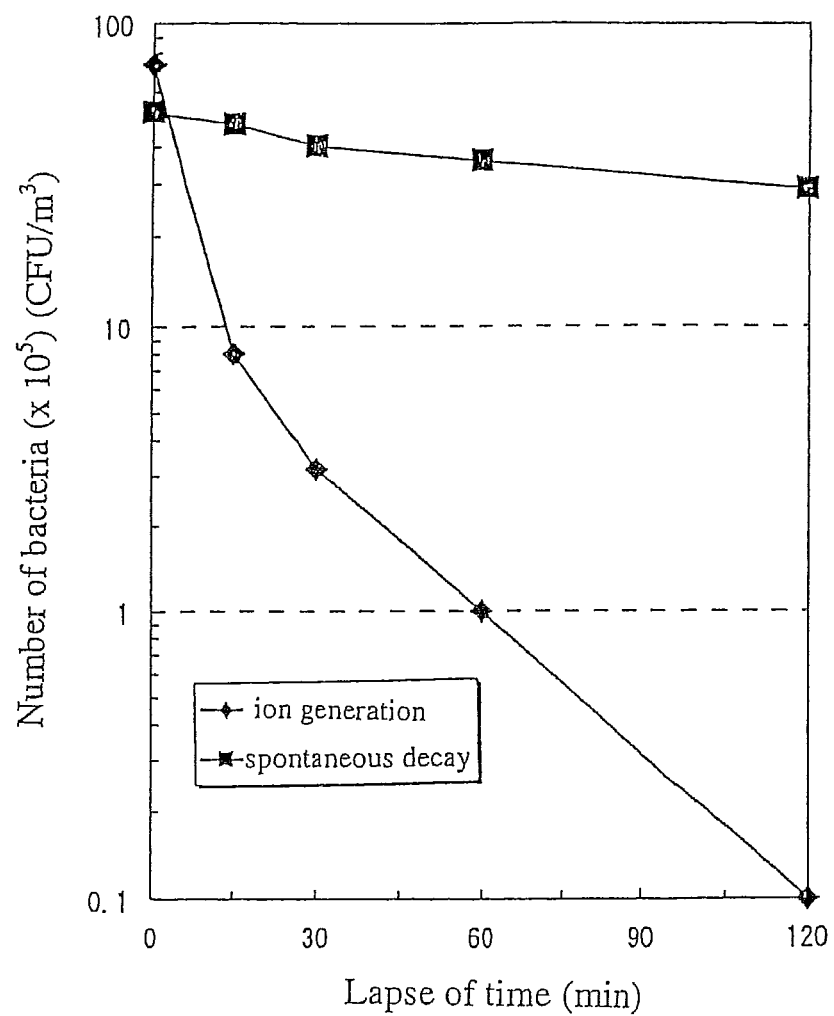
FIG. 19 is a graph showing the change with time of the concentration of aerial suspended Bacillus bacteria at the ion concentration of 200,000 N/cm$^3$ of Example 8.
Figure 20:
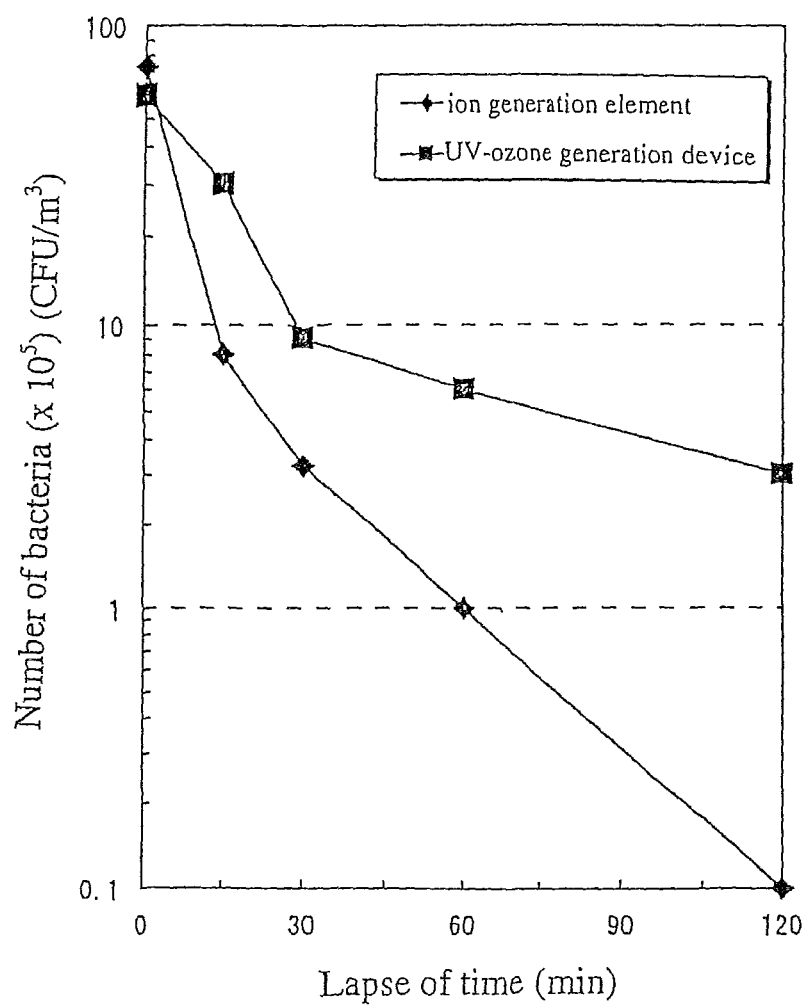
FIG. 20 is a graph showing the change with time of the concentration of aerial suspended Bacillus bacteria by an ion generation element and a UV-ray ozone generation device of Example 8.

FIG. 19 is a graph showing the change with time of the concentration of aerial suspended Bacillus bacteria at an ion concentration of 200,000 N/cm$^3$. The same ion generation device as in Example 6 was used. FIG. 20 is a graph showing the change with time of the concentration of aerial suspended Bacillus bacteria by the ion generation element and by the UV-ray ozone generation device. For demonstrating the effect of the ion generation element for eliminating suspended Bacillus bacteria existing in a predetermined space, an FRP container with a space of 1 m$^3$ of 1 m×1 m×1 m size, having acrylic plates attached to both ends, was used in this test. Inside the container, the ion generation element was attached at a portion of an upper air blow port of a blower at an air flow of 8 m$^3$/min.

Further, for suspending the sprayed bacteria for a long time, axial flow blowers 4 each of 15 cm square were placed by four units at four corners of the container such that the air blow was directed upward. The injection tube 5 for spraying bacteria solution was disposed at one end of the acrylic plate of the container 8, which was used as a test apparatus.

The test bacteria were inoculated on a nihon-coseibussitsu kijun sporulation medium (Nihon Kosei Bussitsu Iyakuhin Kijun, notification No. 117 of Ministry of Health and Welfare No. 117, Jun. 30, 1982) and cultured at 35° C. for seven days. After washing the bacteria with sterilized physiological saline, they were heat-treated at 65° C. for 30 min to confirm sporulation by a microscope. They were washed and diluted with sterilized physiological saline and used as a spore solution.

The test bacteria solution was charged by 10 ml to a glass atomizer, which was connected to one end of the test apparatus. A glass impinger incorporated with 100 ml of sterilized physiological saline was connected to the other end. In the atomizer, the discharged pressure of pressurized air from an air compressor was controlled to be 0.48 hPa by a gauge pressure and the test bacteria were sprayed from a spray port. The amount of spray was adjusted to be 1.0 ml (spray flow rate 0.1 ml/min×spray time 10 min). The axial flow blower 4 was operated at the same time with the spraying of the bacteria solution and operated continuously to the end of the test.

At the instance the spray was completed, the air in the container was sucked and collected by the impinger at a suction flow rate of 10 L/min for 10 min. This was defined as 0 min value. In the case of operating the ion generation element 1, the ion generation element 1 and the blower 4 were operated simultaneously. After starting the operation and after lapse of a predetermined period of time, the air in the container was sucked and collected by 100 L in the same manner as that for 0 min value. The ion generation concentration was set to be 200,000 $N/cm^3$.

Further, also in the case of not operating the ion generation element (spontaneous decay value), it was operated in a state of operating only the blower 4 without operating the ion generation element and the air in the container was sucked and collected on every lapse of time. The atmosphere in the space was at a temperature of 25° C. and a relative humidity of 60% RH. Further generation of ions was confirmed in a range from a temperature of 0° C. and a relative humidity 10% to a temperature of 40° C. and a relative humidity of 90%.

Further, for conducting a comparative experiment with ozone, a test was conducted by using a UV-ray ozone generation device (OZ51N-1, Sen Tokushu Kogen K.K.) at the same amount of ozone generation amount of 1.637 mg/h (22° C., 17% RH) as the amount of ozone generated from the ion generation element.

A sterilized physiological saline formed by sucking and collecting air in the container by the impinger was used as a test solution, which was diluted stepwise by using sterilized physiological saline, and the stock solution and each of the diluted solutions were coated on the Trypticase Soy Agar medium (BBL) and cultured at 35° C. for 48 hours. After culturing, the number of colonies grown on the medium was counted and indicated by the number of cells per sucked air.

As shown in FIG. 19, compared with the case of not operating the ion generation element, it was confirmed that the concentration of the suspended bacteria after lapse of 30 min was decreased to about 1/10 when the ions were generated compared with the case of not operating the ion generation element. Further, after lapse of 120 min, suspended bacteria were no more detected.

As shown in FIG. 20, compared with the case of UV-ray ozone generation device, it was confirmed that the concentration of suspended bacteria was decreased to about ½ after lapse of 60 min by the ion generation element compared with the UV-ray ozone generation device. Accordingly, the sterilizing effect was confirmed by the effect described in Example 6 also for Bacillus bacteria which formed heat resistant spores. The effect can be expected also for anthrax bacteria since they are of an identical genus with Bacillus bacteria.

Example 9

Figure 21:
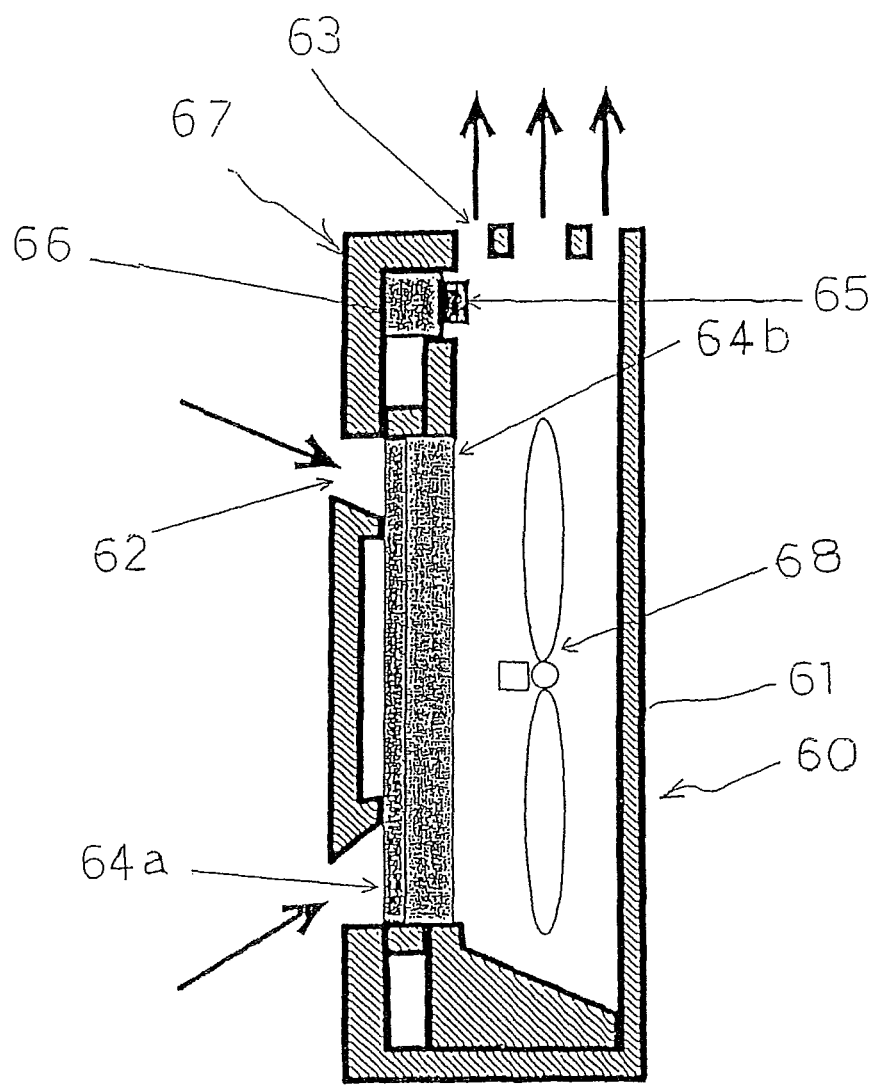
FIG. 21 is a cross sectional view of an air conditioner in which an ion generation element of Example 9 is disposed at a blowing port channel.
Figure 22:
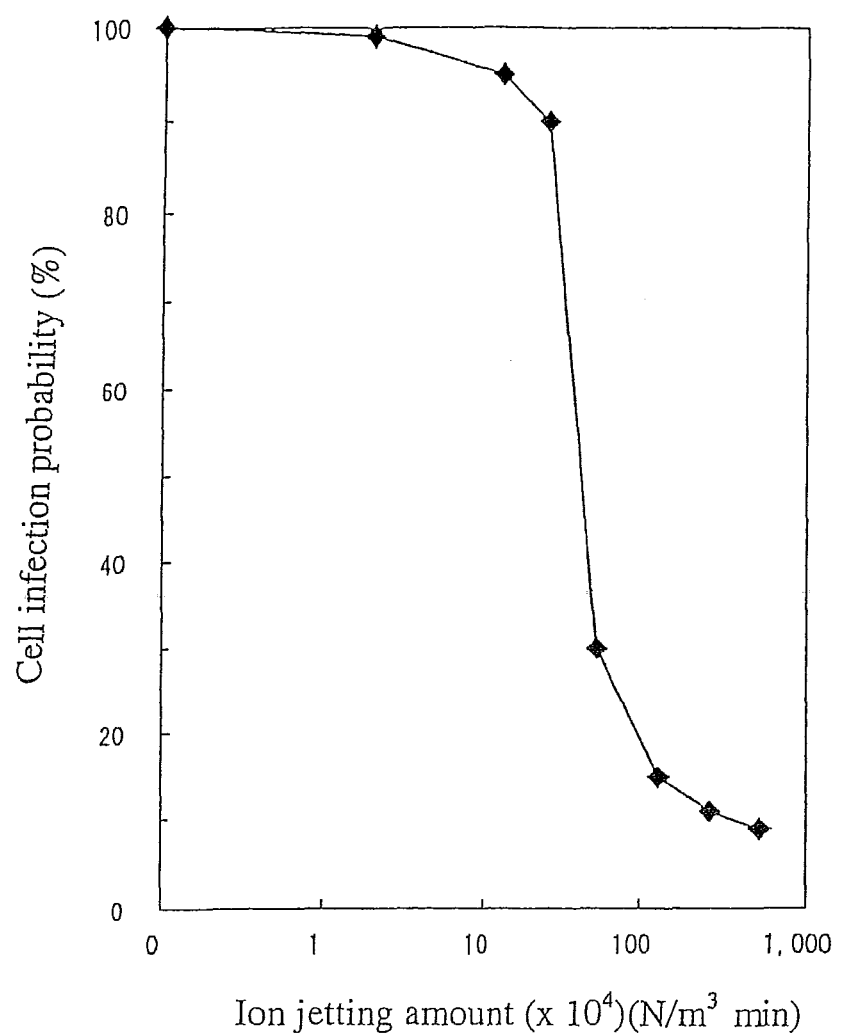
FIG. 22 is a graph showing the cell infection probability of aerial suspended viruses depending on the ion jetting amount of Example 9.
Figure 23:
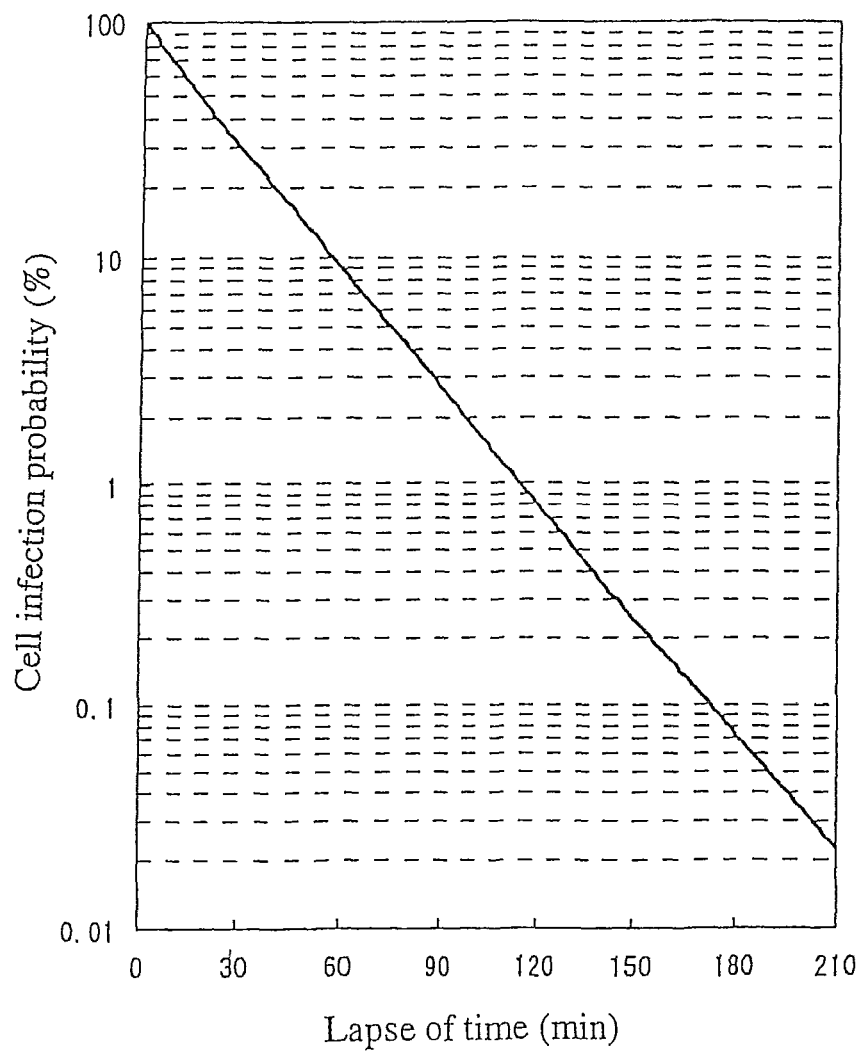
FIG. 23 is a graph showing the change with time of an aerial viruses cell infection probability depending on ion jetting of Example 9.

FIG. 21 shows a cross sectional view of an air conditioner disposed at a blowing channel of an ion generation element. FIG. 22 is a graph showing the cell infection probability of aerial suspended viruses after 60 min against the jetting amount of ions to the space with a 27 liter capacity. FIG. 23 is a graph showing the change with time of the infection probability of aerial viruses to the cells in a case of supplying positive and negative ions each at 5,400,000 $N/m^3$ for one min to a space with a 30 $m^3$ capacity.

In the test shown in FIG. 22, for demonstrating the effect of reducing the cell infection rate of the suspended influenza viruses existing in the space depending on the jetting amount of ions, the vinyl chloride container with a space of 27 L of 30 cm×30 cm×30 cm size, having a viruses sprayer and a collection device attached to both ends thereof, was used. Inside the container, the ion generation element was attached at a portion of the blow port above the blower. Further, with an aim of suspending the sprayed viruses for a long period of time, an axial flow blower was disposed such that air blow was directed upward.

Influenza viruses (A(H1N1) A/JPR8/34: ATCC VR-95) were inoculated to an allantoic membrane cavity of a embryonated egg and cultured in an incubator, and the allantoic liquid was sampled and used as a test viruses solution. The test viruses solution was put by 10 ml into a glass atomize, and the glass atomizer was connected to one end of the test apparatus. A glass impinger in which 10 ml of sterilized physiological saline was incorporated was connected to the other end. In the atomizer, the discharge pressure of the pressurized air from an air compressor was controlled to be 0.48 hPa by gauge pressure and the test viruseses was sprayed from the spray port. The spray amount was set to 3.0 ml (spray flow rate 0.1 ml/min×spray time 30 min). The axial flow blower was operated simultaneously with the spray of the viruses solution and operated continuously to the end of the test.

At the instance the spray was completed, air in the container was sucked and collected by the impinger at a suction flow rate of 10 L per min for 30 min. This was defined as 0 min value. After lapse of one hour after starting the operation, the air in the container was sucked and collected in the same manner as that for 0 min value. PBS(−) formed by sucking and collecting the air in the test apparatus via the impinger was used as a test solution and the influenza viruses was measured by a plaque method using MDCK cells. The ion jetting amount was controlled by controlling the input voltage to the ion generation element. Assuming the cell infection probability to be 100% in the case of the jetting amount of positive and negative ions each at 0/$m^3$ min, rapid lowering of the cell infection probability was confirmed at 270,000 $N/m^3$ min or more, and the effect of lowering the infectivity of viruses was confirmed at the jetting amount of positive and negative ions each at 270,000 $N/m^3$ min or more.

Further, for confirming the effect in the space actually used in the residential circumstance, the air conditioner 60 shown in FIG. 21 was disposed in a space capacity of 30 $m^3$ in the test shown in FIG. 23, and the residual ratio of the suspended viruses in the space is shown in the case of operating the ion generation element 65, from which a dust collection filter 64b and a deodoring filter 64a were detached.

Referring to the constitution of the air conditioner 60 shown in FIG. 21, an air suction port 62 is formed at the frontal surface of an indoor unit 61 and an air blow port 63 is formed at the upper surface of the unit 61. A deodoring filter 64a and a dust collecting filter 64b are provided at the suction port 62, and an ion generation device 67 comprising an ion generation element 65 and a high voltage power source 66 therefor is disposed near the air blow port 63. Then, the air sucked from the air suction port 62 by a blower 68 inside the unit is emitted via the air blow port 63. In this case, ionized air is emitted by driving the ion generation device 67.

In air conditioner having the constitution described above, the ion generation element 65 is disposed at the blow channel and, when the air sucked from the suction port 62 is emitted from the blow port 63, ions can be incorporated into the sucked air and emitted into the space. Thus, the ions are added not only to the sucked air but also the ions can be added entirely in the space.

The way of the viruses concentration measurement was the same as that conducted in the test of FIG. 22. The positive and negative ions were supplied each at a jetting amount of 5,400,000 N/m$^3$ for one min. It was confirmed that the cell infection probability was lowered to $1/10$ for one hour.

As has been described above, it was found that the effect of inactivating viruseses in air could be evaluated also in the capacity of the air conditioner used actually in the residential circumstance.

Positive and negative ions delivered to the space surround viruses suspended in air and positive and negative ions generate active species of hydrogen peroxide $H_2O_2$ or radical OH due to chemical reaction at the surface of viruses, thereby destroying and killing proteins. With the method as described above, viruses in air can be effectively sterilized and eliminated.

In this example, ions represent both of positive and negative ions, and concentration of the ions are also described as a mean value for the concentration of each of the ions assuming that they are substantially equal to each other.

Further, throughout the examples described above, the advantageous effects of the present invention can be obtained also by using a method of Lenard effect for the particle releasing method, that is, of jetting a liquid or causing vibrations thereto, thereby separating the same physically into electrically charged particles.

Further, the same effects as those of the present invention can be obtained in a case of using positive ions, negative ions or gases comprising positive and negative ions mixed to each other, as well as charged particles such as α-rays, β-rays, or various kinds of gas particles rendered into the plasma state, particles such as of radicals and particles of chemicals in addition to those described above.

INDUSTRIAL APPLICABILITY

As described heretofore, according to the present the invention, the sterilizing performance of particles such as ions for microorganisms can be measured and evaluated by suspending microorganisms in a given space, allowing sterilizing particles to irradiate the microorganisms and subsequently sampling and measuring the microorganisms.

The invention claimed is:

1. An apparatus for evaluating elimination of microorganisms, comprising:
   a container for carrying out the sterilizing treatment of microorganisms,
   a cylindrical wind tunnel having openings on both sides thereof, provided in the space inside the container, forming a passage of the air containing microorganisms, the passage arranged from one side opening of the cylindrical wind tunnel to the other side opening of the cylindrical wind tunnel,
   a microorganism injection tube, wherein said tube supplies microorganisms in suspension from one side of the wind tunnel,
   an ion generator for irradiating particles for sterilizing treatment of microorganisms to the air containing microorganisms supplied inside the wind tunnel,
   a microorganism sampling tube and microorganism sampler for sampling, from the other side of the wind tunnel, the microorganisms after the sterilizing treatment of microorganisms by the ion generator, wherein measuring the concentration or the activity or the cell infection ratio of the microorganisms sampled by the sampling tube and evaluating the efficiency of the elimination of the microorganisms of the particles are done.

2. The apparatus for evaluating elimination of microorganisms according to claim 1, wherein the particles for sterilizing the microorganisms are positive ions and negative ions generated by ionization of the atmosphere such as discharge in the air.

3. The apparatus for evaluating elimination of microorganisms according to claim 1, wherein the ion generator is disposed inside the cylindrical wind tunnel.

4. The apparatus for evaluating elimination of microorganisms according to claim 1, wherein the ion generator and the sampling tube and microorganism sampler are arranged outside the vertically downward region of the microorganism injection tube.

5. The apparatus for evaluating elimination of microorganisms according to claim 1, wherein a separate container is arranged outside the container so as to cover the container.

6. The apparatus for evaluating elimination of microorganisms according to claim 1, wherein a stirrer for stirring the space inside the container is arranged in the space inside the container.

7. The apparatus for evaluating elimination of microorganisms according to claim 1, wherein the apparatus is constituted such that supplying microorganisms with the microorganism injection tube is done by preparing a solution of microorganisms in dispersion in a mist form and then spraying in a mist form into the space inside the container.

8. The apparatus for evaluating elimination of microorganisms according to claim 1, wherein the particles for the sterilizing treatment of microorganisms are particles generated by any of atmospheric electric discharge, atmospheric irradiation of radiation, and the Lenard effect.

9. The apparatus for evaluating elimination of microorganisms according to claim 1, wherein the particles for the sterilizing treatment of microorganisms are any of radiation, X ray, gamma ray or electromagnetic wave.

10. The apparatus for evaluating elimination of microorganisms according to claim 1, wherein the apparatus is constituted such that the ion generator can irradiate particles of chemicals as the particles for the sterilizing treatment of microorganisms.

* * * * *

UNITED STATES PATENT AND TRADEMARK OFFICE
CERTIFICATE OF CORRECTION

| | |
|---|---|
| PATENT NO. | : 8,828,714 B2 |
| APPLICATION NO. | : 13/495964 |
| DATED | : September 9, 2014 |
| INVENTOR(S) | : Kazuo Nishikawa et al. |

It is certified that error appears in the above-identified patent and that said Letters Patent is hereby corrected as shown below:

IN THE CLAIMS:

Column 26, line 56, immediately after claim 10, insert the following:

--11. A method for evaluating elimination of microorganisms, comprising:
  installing a wind tunnel inside a container to provide the apparatus of claim 1,
  forming a passage of air containing microorganisms inside the wind tunnel,
  supplying the air containing microorganisms having a combination of one or more members selected from the group consisting of bacteria, mycete, viruses and allergens from one side of the wind tunnel,
  irradiating particles for sterilizing treatment of the microorganisms into the inside of the wind tunnel,
  sampling the microorganisms after completion of the irradiation of the particles from the other side of the wind tunnel,
  a sequence of treatments comprising supplying microorganisms, sterilizing microorganisms, and sampling the microorganisms along one pass using the wind tunnel,
  supplying microorganisms under the same conditions for the sterilizing treatment with the irradiation of the particles,
  sampling the microorganisms without the radiation of the particles,
  comparing the concentration or the activity or the cell infection ratio of the microorganisms in the case with the sterilizing treatment of the microorganisms and the case without the sterilizing treatment of the microorganisms, and
  evaluating the efficiency of the elimination of the microorganisms based on the comparison result.
  12. The method for evaluating elimination of microorganisms according to claim 11, wherein positive ions and negative ions generated by ionization of the atmosphere such as discharge in the air are particles for sterilizing treatment of the microorganisms.

Signed and Sealed this
Third Day of February, 2015

Michelle K. Lee
*Deputy Director of the United States Patent and Trademark Office*

CERTIFICATE OF CORRECTION (continued)
U.S. Pat. No. 8,828,714 B2

IN THE CLAIMS (cont):

13. The method for evaluating elimination of microorganisms according to claim 11, wherein measuring the timewise change of the measured microorganisms in an irradiation time period of the particles is also done.

14. The method for evaluating elimination of microorganisms according to claim 11, wherein measuring the dependency of the elimination performance on the particles concentration is also done.

15. The method for evaluating elimination of microorganisms according to claim 11, wherein supplying microorganisms into the space inside the container is done by spraying a solution of microorganisms in dispersion in a mist form.

16. The method for evaluating elimination of microorganisms according to claim 11, wherein the microorganisms can be measured by using cell culture due to the microorganisms, hemagglutination induced by the microorganisms, or allergic reaction induced by the microorganisms.

17. The method for evaluating elimination of microorganisms according to claim 11, wherein the particles for the sterilizing treatment of microorganisms are particles generated by any of atmospheric electric discharge, atmospheric irradiation of radiation, and the Lenard effect.

18. The method for evaluating elimination of microorganisms according to claim 12, wherein the particles for the sterilizing treatment of microorganisms are any of radiation, X ray, gamma ray or electromagnetic wave.

19. The method for evaluating elimination of microorganisms according to claim 11, wherein the particles for the sterilizing treatment of microorganisms are particles of chemicals.--

UNITED STATES PATENT AND TRADEMARK OFFICE
CERTIFICATE OF CORRECTION

| | | |
|---|---|---|
| PATENT NO. | : 8,828,714 B2 | |
| APPLICATION NO. | : 13/495964 | |
| DATED | : September 9, 2014 | |
| INVENTOR(S) | : Kazuo Nishikawa et al. | |

It is certified that error appears in the above-identified patent and that said Letters Patent is hereby corrected as shown below:

On the title page, under abstract "10 Claims, 23 Drawing Sheets" should read --19 Claims, 23 Drawing Sheets--

IN THE CLAIMS:

Column 26, line 56, immediately after claim 10, insert the following:

--11. A method for evaluating elimination of microorganisms, comprising:
installing a wind tunnel inside a container to provide the apparatus of claim 1,
forming a passage of air containing microorganisms inside the wind tunnel,
supplying the air containing microorganisms having a combination of one or more members selected from the group consisting of bacteria, mycete, viruses and allergens from one side of the wind tunnel,
irradiating particles for sterilizing treatment of the microorganisms into the inside of the wind tunnel,
sampling the microorganisms after completion of the irradiation of the particles from the other side of the wind tunnel,
a sequence of treatments comprising supplying microorganisms, sterilizing microorganisms, and sampling the microorganisms along one pass using the wind tunnel,
supplying microorganisms under the same conditions for the sterilizing treatment with the irradiation of the particles,
sampling the microorganisms without the radiation of the particles,
comparing the concentration or the activity or the cell infection ratio of the microorganisms in the case with the sterilizing treatment of the microorganisms and the case without the sterilizing treatment of the microorganisms, and
evaluating the efficiency of the elimination of the microorganisms based on the comparison result.

This certificate supersedes the Certificate of Correction issued February 3, 2015.

Signed and Sealed this
Tenth Day of March, 2015

Michelle K. Lee
*Deputy Director of the United States Patent and Trademark Office*

CERTIFICATE OF CORRECTION (continued)  
U.S. Pat. No. 8,828,714 B2

IN THE CLAIMS (cont):

12. The method for evaluating elimination of microorganisms according to claim 11, wherein positive ions and negative ions generated by ionization of the atmosphere such as discharge in the air are particles for sterilizing treatment of the microorganisms.

13. The method for evaluating elimination of microorganisms according to claim 11, wherein measuring the timewise change of the measured microorganisms in an irradiation time period of the particles is also done.

14. The method for evaluating elimination of microorganisms according to claim 11, wherein measuring the dependency of the elimination performance on the particles concentration is also done.

15. The method for evaluating elimination of microorganisms according to claim 11, wherein supplying microorganisms into the space inside the container is done by spraying a solution of microorganisms in dispersion in a mist form.

16. The method for evaluating elimination of microorganisms according to claim 11, wherein the microorganisms can be measured by using cell culture due to the microorganisms, hemagglutination induced by the microorganisms, or allergic reaction induced by the microorganisms.

17. The method for evaluating elimination of microorganisms according to claim 11, wherein the particles for the sterilizing treatment of microorganisms are particles generated by any of atmospheric electric discharge, atmospheric irradiation of radiation, and the Lenard effect.

18. The method for evaluating elimination of microorganisms according to claim 12, wherein the particles for the sterilizing treatment of microorganisms are any of radiation, X ray, gamma ray or electromagnetic wave.

19. The method for evaluating elimination of microorganisms according to claim 11, wherein the particles for the sterilizing treatment of microorganisms are particles of chemicals.--